United States Patent
Pang et al.

(10) Patent No.: US 9,920,020 B2
(45) Date of Patent: Mar. 20, 2018

(54) USING SQUARAINE DYES AS NEAR INFRARED FLUORESCENT SENSORS FOR PROTEIN DETECTION

(75) Inventors: Yi Pang, Copley, OH (US); Yongqian Xu, Yangling (CN)

(73) Assignee: The University of Akron, Akron, OH (US)

( * ) Notice: Subject to any disclaimer, the term of this patent is extended or adjusted under 35 U.S.C. 154(b) by 1235 days.

(21) Appl. No.: 13/459,837

(22) Filed: Apr. 30, 2012

(65) Prior Publication Data

US 2012/0276642 A1 Nov. 1, 2012

Related U.S. Application Data

(60) Provisional application No. 61/480,631, filed on Apr. 29, 2011.

(51) Int. Cl.
- *G01N 33/68* (2006.01)
- *G01N 21/64* (2006.01)
- *C07D 417/14* (2006.01)
- *C07D 277/64* (2006.01)
- *C09B 57/00* (2006.01)

(52) U.S. Cl.
CPC ......... *C07D 277/64* (2013.01); *C07D 417/14* (2013.01); *C09B 57/007* (2013.01); *G01N 33/6839* (2013.01); *G01N 2021/6495* (2013.01)

(58) Field of Classification Search
None
See application file for complete search history.

(56) References Cited

U.S. PATENT DOCUMENTS

| | | | |
|---|---|---|---|
| 8,273,329 B2* | 9/2012 | Zhao | C07D 209/12 424/9.6 |
| 2010/0044230 A1* | 2/2010 | Papadimitrakopoulos et al. | 204/547 |
| 2011/0118459 A1* | 5/2011 | Smith | C07D 403/12 540/465 |

OTHER PUBLICATIONS

Xu et al. "Host-guest assembly of squaraine dye in cucurbit[8]uril: its implication in fluorescent probe for mercury ions," Chem. Commun., 2010, 46, 4073-4075; published online Apr. 20, 2010.*
Yefimova et al. "Effects of surfactants on the molecular aggregation of squaraine dye Sq-2Me in aqueous solutions," Functional Materials 16, No. 4, 2009, 460-465.*
Volkova, K. D. et al. "Aza-substituted squaraines for the fluorescent detection of albumins," Dyes and Pigments, vol. 90, Issue 1, Jul. 2011, pp. 41-47; Available online Nov. 18, 2010.*
Jisha, V. S.; et al.; J. Phys. Chem. B 2010, 114, 5912-5919.
Jisha, V. S.; et al.; J. Am. Chem. Soc. 2006, 128, 6024-6025.
Volkova, K. D.; et al.; Dyes and Pigments 2007, 72, 285-292.
(Continued)

*Primary Examiner* — Yelena G Gakh
*Assistant Examiner* — Michelle Adams
(74) *Attorney, Agent, or Firm* — Renner Kenner Greive Bobak Taylor & Weber

(57) ABSTRACT

Squaraine dyes are used to detect the presence of protein in a test sample, which is a substance that may contain protein. A squarine dye is placed in water, and in some instances joined with an aggregation agent, to create an aqueous dye solution. That dye solution is joined with a test sample. When the dye solution is joined with the test sample and the resultant test solution is excited by the application of photons, a resulting fluorescence or absence thereof reveals if protein was present in the test sample.

15 Claims, 14 Drawing Sheets

(56) References Cited

OTHER PUBLICATIONS

Wang, B.; et al.; X. Dyes and Pigments 2010, 85, 43-50.
Xu, Yongqian.; et al.; J. Phys. Chem. B 2010, 114, 8574-8580.
Xu, Yongqian.; et al.; Chem. Commun., 2011, 47, 6662-6664.
Patsenker, Leonid.; et al. Ann. N.Y. Acad. Sci. 1130: 179-187 (2008).
Suzuki, Yoshio.; et al.; Chem. Int. Ed. 2007, 46, 4097-4099.
Tatikolov, Alexander S.; Journal of Photochemistry and Photobiology C: Photochemistry Reviews 13 (2012) 55-90.
Volkova, K. D.; et al.; J Fluoresc (2008) 18:877-882.

* cited by examiner

USING SQUARAINE DYES AS NEAR INFRARED FLUORESCENT SENSORS FOR PROTEIN DETECTION

FIELD OF THE INVENTION

The present invention generally relates to compounds for the detection of proteins, compositions for the detection of proteins, and methods for detecting proteins.

BACKGROUND OF THE INVENTION

Protein detection is of profound importance in clinical research. Traditional methods of detecting proteins are generally based on absorption spectrometry, such as Bradford method and Lowry method, which involve complicated steps and have limited sensitivity with narrow linear response range. Fluorescence detection of proteins offers an attractive alternative method, which exhibit high sensitivity and fast response. Fluorescent detection is widely used in modern biomedical techniques for analysis and quantification of proteins.

It is the presence, abundance and activity of protein that controls cell function and disease. Clinical research requires protein profiling techniques which reveal characteristic protein patterns that can be compared between normal and diseased states to improve diagnosis and prognosis. Since the abnormal protein levels is related to the early disease, the protein levels can be an invaluable tool for early disease detection, which likely leads to effective treatments on patients in alleviating or stabilizing the disease process. For clinical applications, it is highly desirable to develop fluorescent probes that can quantify the protein concentration in a cost-effective manner.

For efficient drug delivery and therapeutic application, it is essential to discover site-selective and protein-selective fluorescent probes for BSA. Few BSA-selective fluorescent sensors are available and most of them are chosen from molecule library developed with major synthetic efforts

SUMMARY OF THE INVENTION

One embodiment of this invention provides a squaraine dye defined by the formula:

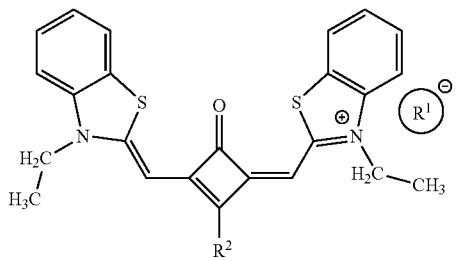

wherein $R^1$ is a counterion and $R^2$ is selected from the group consisting of

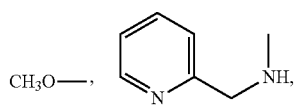

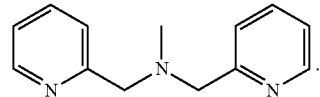

Another embodiment provides a squaraine dye defined by the formula:

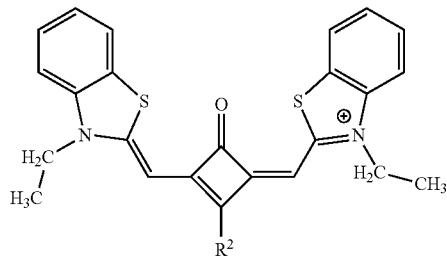

wherein $R^2$ is selected from the group consisting of:

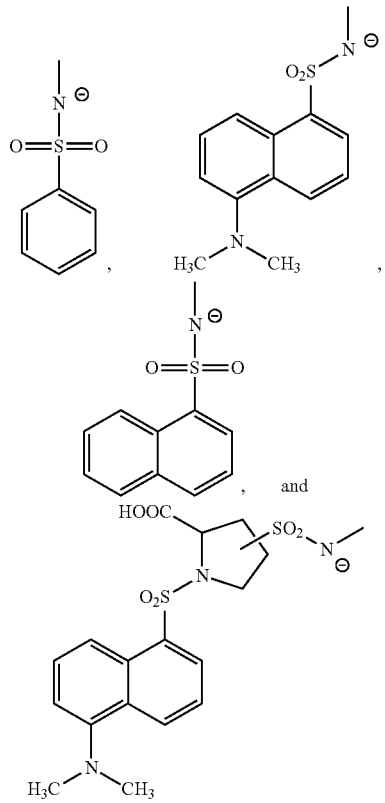

Yet another embodiment provides a composition for the detection of protein comprising: an aggregation agent; and a squaraine dye.

This invention also provides a method for the detection of protein in a test sample, wherein a test sample is a substance to be tested to determine if there is a protein therein, the method comprising the steps of: preparing a dye solution comprising a squaraine dye and an aggregation agent, joining the dye solution with a test sample, and exciting the test solution at a wavelength of about 635 nm to about 650 nm.

DETAILED DESCRIPTION OF ILLUSTRATIVE EMBODIMENTS

Figure 1:
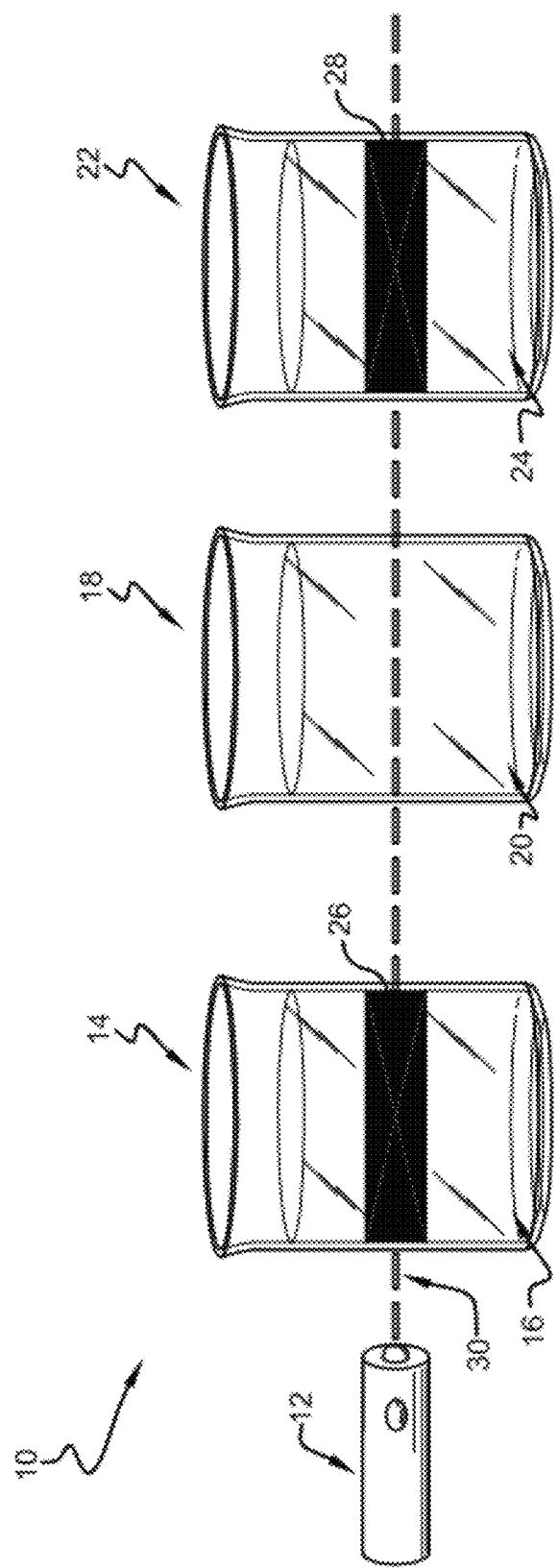
FIG. 1 is a general schematic of a method for testing one or more test solutions for the presence of protein in accordance with this invention.

In one or more embodiments, the invention relates to squaraine dyes for the detection of proteins. In other embodiments, the invention relates to compositions for the detections of proteins. In still other embodiments, the invention relates to methods for the detection of proteins using squaraine dyes.

Squaraine (SQ) represents an interesting class of dyes, which bear a positive charge and a give sharp and intense absorption and fluorescence in the red to near-infrared region. In solution, SQ dyes are known to be spontaneously assembled into an ordered structure, with chromophores either in a parallel-oriented fashion (H-aggregate) or in a head-to-tail arrangement (J-aggregates). The different form of aggregates often affects the optical absorption and emission properties of SQ. The J-aggregates give red-shifted absorption bands and enhanced luminescence (as compared to monomer), while H-aggregates exhibit blue shifted absorption bands and poor emission. Typically, SQ exhibits a mixture of H- or J-aggregates when in solution.

While being non-fluorescent in the aggregate state, squaraine dyes exhibit fluorescence when in a monomeric form, wherein it should be understood that the "monomeric form" as used herein is to connote that the squaraine dyes have disassociated from their aggregate forms, i.e., become substantially non-aggregated. In other words, the squaraine dyes exhibits fluorescence when it is not substantially packed in an aggregate form.

It has been discovered that many certain proteins, including Bovine Serum Albumin, have the ability to dissociate squaraine dyes from the H- and J-aggregate states thereby allowing them to assume the monomeric form and exhibit fluorescence when excited by photons at certain wavelengths, typically between 400 and 700 nanometers (nm). This may be referred to as protein-induced fluorescence. The present invention takes advantage of the dissociation of the squarine dyes from their aggregated states in the presence of proteins in order to provide a test for determining if certain proteins are present in solution.

In one or more embodiments, squaraine dyes may be used to detect the presence of protein in a test sample. A test sample is a substance, typically a liquid, that may contain protein. A squaraine dye and an aggregation agent are joined in water to create what is termed herein an aqueous dye solution and that dye solution is joined with a test sample. The aggregation agent serves to promote the formation of aggregates of the squarine dye in the dye solution, thereby suppressing any fluorescence background upon excitation by the application of photons of certain wavelengths. In other words, the aggregation agent lowers the baseline fluorescence by promoting the aggregate state of the squaraine dye. When the dye solution is joined with the test sample and the resultant test solution is excited by the application of photons, a resulting fluorescence or absence thereof will reveal if protein was present in the test sample. More particularly, if protein is present in the test sample, then the joining of the dye solution and test sample will cause the squaraine dyes to dissociate from their aggregate form (due to the presence of the protein) and the joined solution will exhibit fluorescence when excited. If protein is not present in the test sample the squaraine dyes will remain in the aggregated state and the squaraine dyes will not exhibit fluorescence when excited.

Examples of test samples include, but are not limited to, blood, urine, lacrimal fluid (tears), homogenized tissue, homogenized plant matter, homogenized cells, purified proteins, waste water, drinking water, and environmental water. These all may include proteins that would be beneficial to detect in accordance with this invention.

In one or more embodiments the aggregation agent may be an anionic surfactant. In the absence of protein a solution comprising a squaraine dye and an anionic surfactant will not exhibit fluorescence, because the squaraine dye will be in the aggregate form. In the presence of protein a solution comprising a squaraine dye and an anionic surfactant will exhibit fluorescence, because the squaraine dye will dissociate from the aggregate form.

Exemplary anionic surfactants include, but are not limited to, sodium dodecyl sulfate (SDS), sodium dodecyl benzene sulfonate (SDBS), tetraethylammonium dodecylbenzenesulfonate (DBS), and dioctyl sodium sulfosuccinate (DSS).

The amount of anionic surfactant used can be defined in terms of percent of critical micelle concentration. In one or more embodiments, the amount of anionic surfactant is 1% to 95% of the critical micelle concentration. In other embodiments, the amount of anionic surfactant is 5% to 50% of the critical micelle concentration. In still other embodiments, the amount of anionic surfactant is 15% to 25% of the critical micelle concentration.

The amount of anionic surfactant used can also be defined in terms of percent weight of solution. In one or more embodiments, the amount of anionic surfactant in solution is 0.002% to 0.23%. In other embodiments, the amount of anionic surfactant in solution is 0.01% to 0.12%. In still other embodiments, the amount of anionic surfactant in solution is 0.03% to 0.06%.

In one or more embodiments the aggregation agent may be a chemically converted graphene, particularly a graphene oxide. The chemically converted graphene is a graphene oxide where the number of oxygen functional groups is reduced. The number of oxygen function groups can be reduced, for example, by chemical reduction using hydrazine. The planar graphene allows the dye molecules to be easily assembled as aggregates on the graphene surface. The residual oxygen in the reduced graphene can be about 7-15% oxygen by weight, in order to have certain water solubility.

The amount of graphene oxide used can also be defined in terms μg/mL. In one or more embodiments, the amount of graphene oxide in solution is to 1 to 20 μg/mL. In other embodiments, the amount of graphene oxide in solution is 2 to 10 μg/mL. In still other embodiments, the amount of graphene oxide in solution is 3 to 7 μg/mL, and, in yet other embodiments, 4 to 5 μg/mL.

Graphene oxide can be purchased comercially. Additionaly, graphene oxide can be prepared according to the Hummer's Method detailed in W. S. Hummers Jr. and R. E. Offeman, *J. Am. Chem. Soc.,* 1958, 80, 1339 which is incorporated herein by reference.

In one or more embodiments, squaraine dye used in combination with an aggregation agent may be represented by the following formula I:

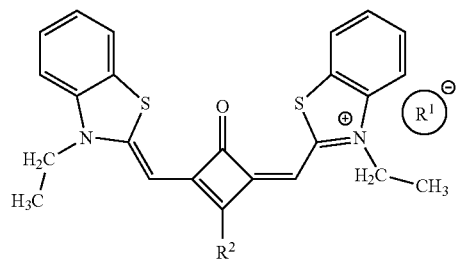

wherein $R^1$ is a counterion and $R^2$ is selected from the group consisting of

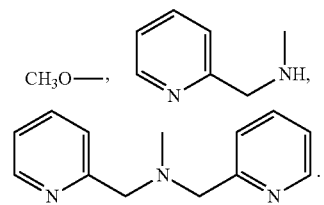

Exemplary types of counterions ($R^1$) include, but are not limited to, trifluoromethanesulfonate ($CF_3SO_3^-$) and iodide ($I^-$).

The squarine dyes may be synthesized according to the methods in Santos, P.; Reis, L. V.; Duarte, I.; Serrano, J. P.; Almeida, P.; Oliveira, A.; Ferreira, L. F. V. *Helvetica Chimica Acta* 2005, 88, 1135-1143 which is incorporated herein by reference. The $R^2$ groups, such as $R^2$=—$OCH_3$, can be easily changed into various amines by substitution. An example is shown below.

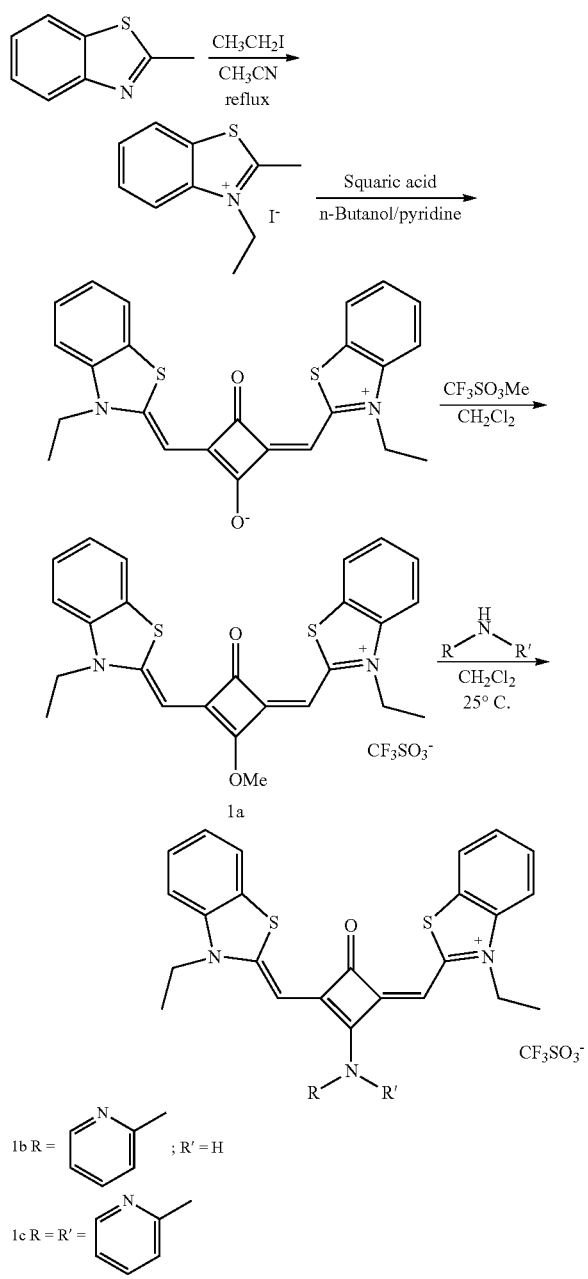

The amount of squaraine dye used to detect protein can also be defined in terms of μM. In one or more embodiments, the amount of squaraine dye in solution is 0.1 μM to 15 μM. In other embodiments, the amount of squaraine dye in solution is 1 μM to 10 μM. In other embodiments, the amount of squaraine dye in solution is 2 μM to 7 μM. In still other embodiments, the amount of squaraine dye in solution is 3 μM to 6 μM. In still other embodiments, the amount of squaraine dye in solution is about 5 μM.

In one or more embodiments, the squaraine dye has a fluorescence response in the near infrared region. In these or other embodiment the squaraine dye has a fluorescence response in the range of about 640 to about 700 nm. In still other embodiments the squaraine dye has a fluorescence response at about 690 nm.

In one or more embodiments, the squaraine dye has an absorbance maxima from about 635 nm to about 650 nm. In these or other embodiments, the squaraine dye may be excited with a red laser pointer.

The general method for employing the squaraine dyes to detect proteins has been disclosed above, but is revisited here. A dye solution is made by joining an aggregation agent and a squaraine dye in water. The aggregation agent promotes the formation of squaraine dye aggregates, which do not exhibit fluorescence. A test sample is joined with the dye solution to form a test solution. Notably, the test sample is a sample (for example urine, blood or tears) that may or may not contain a protein to be detected. For example, the existence of proteins in urine (proteinuria) may be an indicator of kidney disease, so a test sample of urine may be tested for the presence of proteins. The resultant test solution (test sample+dye solution) can be tested for the presence of protein simply by the application of photons, particularly through the use of inexpensive lasers emitting light at wavelengths of from 630 to 670 nm, the most common commercially available red lasers emitting light at about 650 and 671 nm.

One advantage of this method is that it can be used to test a large number of test solutions all at the same time. This is shown in FIG. 1, showing a method 10, wherein a laser 12 directs light 30 (a stimulated emission of photons) through a first container 14 holding a test solution 16, a second container 18 holding a test solution 20 and a third container 22 holding a test solution 24. As seen, the first container 14 and third container 28 hold test solutions 16 that include protein, because the light 30 causes fluorescence as at 26 (container 14) and 28 (container 22). The second container 18 does not show fluorescence and thus, the test sample placed therein to create the test solution 20 did not include protein.

In one or more embodiments, the squaraine dye may be used to detect the presence of protein in vivo. The squaraine dye may be added in vivo, for example, by injecting the squaraine dye into living cells, or treating a portion of water containing an aquatic animal with a squaraine dye. If protein is present in vivo the squaraine dyes will dissociate from aggregates and exhibit fluorescence when excited. If protein is not present in vivo the squaraine dyes will remain in the aggregated state and the squaraine dyes will not exhibit fluorescence when excited. Notably, chemically converted graphene has not cytotoxicity in vivo, so it may be employed as an aggregation agent for in vivo testing. When the aggregation agent is an anionic surfactant it is necessary to choose one that is not toxic.

In another embodiment of this invention, a site selective squaraine dye is employed in a dye solution in order to test for the presence of protein in a test sample. A site selective squaraine dye is a squaraine dye that includes a site selective ligand. A site selective ligand is a molecule that is selective for a specific protein binding site on a protein of interest. In the absence of the protein of interest the site selective squaraine dye will remain assemble into H- or J-aggregates in a dye solution. In the presence of a protein of interest in a test solution, the site selective squarine dye will dissociate from the aggregate form due to the affinity between the site selective ligand the specific protein binding site on the protein of interest.

In one or more embodiments, the protein of interest may be bovine serum albumin (BSA) or a homolog of bovine serum albumin. In these or other embodiments, the specific protein binding site on a protein of interest may be site I on bovine serum albumin or a homolog of bovine serum albumin. In other embodiments, the specific protein binding site on a protein of interest may be site II on bovine serum albumin or a homolog of bovine serum albumin.

The association of the site selective ligands to serum albumins originates from the presence of two major and structurally different binding sites, namely, site I and site II. The binding affinity of site I is mainly driven by hydrophobic interaction, while that of site II by a combination of hydrophobic, hydrogen bonding, and electrostatic interactions. For efficient drug delivery and therapeutic application, it is essential to discover site-selective and protein-selective fluorescent probes for BSA. Our result shows that the DNSA-SQ can bind specifically to site I.

As previously mentioned, a site selective squaraine dye may be prepared by attaching a site selective ligand to a squaraine dye.

In one or more embodiments, the site selective squaraine dye is represented by the following formula I:

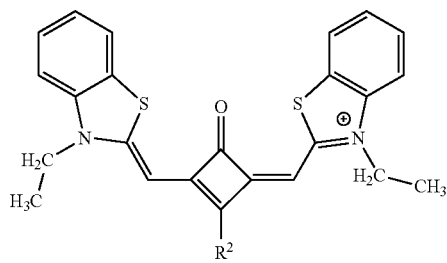

wherein $R^2$ is selected from the group consisting of

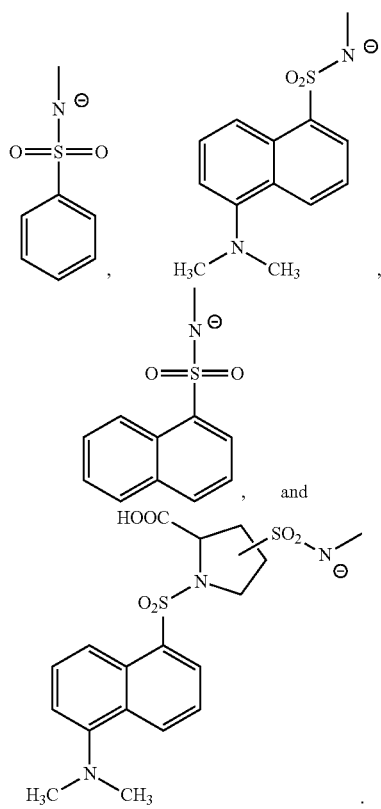

Notably, the $R^2$ group includes a negative charge. In these embodiments the site selective squaraine dye will have a net charge of zero and can be referred to as a zwitterionic squaraine dye. While not wishing to be bound to a particular theory or hypothesis, it is believed that the zwitterionic molecules likely minimize the interaction with serum proteins by charge shielding. In particular embodiments it is believed that the zwitterionic molecules will have a reduced dependence on protein surface charge and could favor hydrophobic interactions to enhance the BSA or BSA homolog site I selectivity.

Dansylamide (DNSA) is site selective for serum albumin site I. DNSA is represented by the formula:

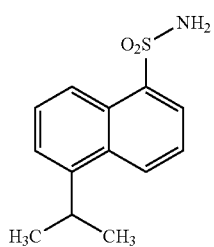

and, as previously described, can be attached to the squaraine dye to provide the corresponding $R^2$ group:

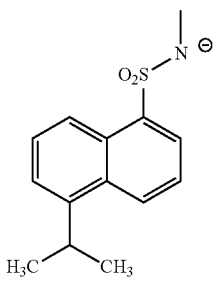 [SMILES: C[N-]S(=O)(=O)c1cccc2c(C(C)C)cccc12]

A site selective (zwitterionic) squaraine dye with an attached dansylamide ligand may be referred to as DNSA-SQ.

Additionally, dansylproline (DP) is site selective for the serum albumin site II. DP is represented by the formula:

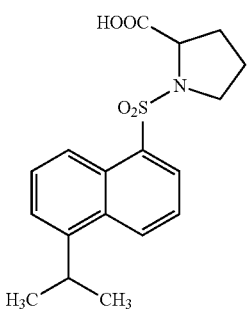 [SMILES: CC(C)c1cccc2c(S(=O)(=O)N3CCCC3C(=O)O)cccc12]

Dansylproline can be attached to the base squaraine structure (as above) with the incorporation of additional moieties as below, such that the $R^2$ group would take the following form:

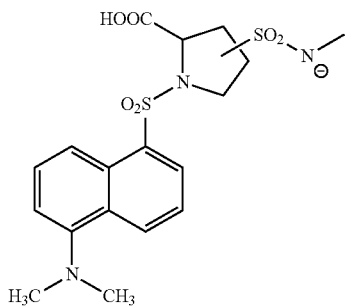

A site selective (zwitterionic) squaraine dye with an attached dansylproline ligand may be referred to as DP-SQ.

In one or more embodiments, the site selective squaraine dyes are used to detect protein in combination with an aggregation agent, substantially as disclosed above.

The amount of site selective squaraine dye used to detect protein can also be defined in terms of μM. In one or more embodiments, the amount of squaraine dye in solution is 0.1 μM to 15 μM. In other embodiments, the amount of squaraine dye in solution is 1 μM to 10 μM. In other embodiments, the amount of squaraine dye in solution is 2 μM to 7 μM. In still other embodiments, the amount of squaraine dye in solution is 3 μM to 6 μM. In still other embodiments, the amount of squaraine dye in solution is about 5 μM.

In one or more embodiments, the site selective squaraine dye has a florescence fluorescence response in the near infrared region. In these or other embodiment the squaraine dye has a fluorescence response in the range of about 640 to about 700 nm. In still other embodiments the squaraine dye has a fluorescence response at about 690 nm.

In one or more embodiments, the site selective squaraine dye has an absorbance maxima from about 635 nm to about 650 nm. In these or other embodiments, the site selective squaraine dye may be excited with a red laser pointer.

The site selective squaraine dye is used to create a dye solution and test a test sample as already disclosed above, and can be used in the method of FIG. 1.

In one or more embodiments, the site selective squaraine dye may be used to detect the presence of protein in vivo. The squaraine dye may be added in vivo, for example, by injecting the squaraine dye into living cells, or treating a portion of water containing an aquatic animal with a squaraine dye. If protein is present in vivo the squaraine dyes will dissociate from aggregates and exhibit fluorescence when excited. If protein is not present in vivo the squaraine dyes will remain in the aggregated state and the squaraine dyes will not exhibit fluorescence when excited. Notably, chemically converted graphene has not cytotoxicity in vivo, so it may be employed as an aggregation agent in in vivo testing. When the aggregation agent is an anionic surfactant it is necessary to choose one that is not toxic.

EXAMPLES

Experimental Results for Compositions of SQ Dyes and Anionic Surfactants

In this experiment, reference is made to squaraine dyes 1a, 1b and 1c. These squaraines are defined below:

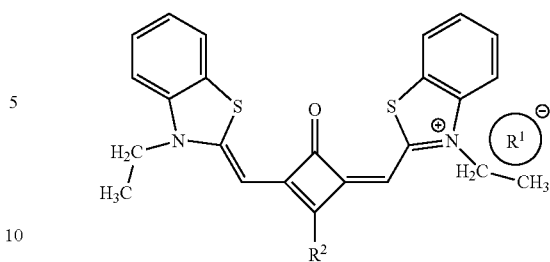

wherein, for squaraine 1a, $R^2$ is —$CH_3O$; for squaraine 1b, $R^2$ is:

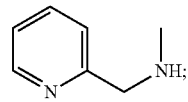

and for squaraine 1c, $R^2$ is:

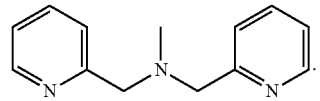 [SMILES: CN(Cc1ccccn1)Cc1ccccn1]

The counterion $R^1$ is $CF_3SO_3^-$.

Reagents

All chemicals and reagents were used directly as obtained commercially unless otherwise noted. Water used was ultra filter deionized and purchased from Fisher Scientific. BSA (≥98%), borax-boric acid, sodium dodecyl sulfate (SDS, electrophoresis grade) were purchased from Acros Chemical, lysozyme, trypsin, formaldehyde dehydrogenase were purchased from SIGMA; and Thrombin was purchased from GE Healthcare.

Spectroscopic Measurements

NMR spectra were collected on a Varian 300 Gemini spectrometer. Mass spectrometric data were obtained on a HP1100LC/MSD mass spectrometry. HRMS data were performed on a TOF MS system. UV-Vis spectra were acquired on a Hewlett-Packard 8453 diode-array spectrometer. Fluorescence spectra were obtained on a HORIBA Jobin Yvon NanoLog spectrometer. The quantum yield of fluorescence of the sample was measured using bis(3-ethylbenzothiazol-2-ylidene)squaraine in ethanol (Φ=0.21) as a standard and calculated using equation (1):

$$\Phi_{unk} = \Phi_{std} \times \left(\frac{I_{unk}}{I_{std}}\right) \times \left(\frac{A_{std}}{A_{unk}}\right) \times \left(\frac{\eta_{unk}}{\eta_{std}}\right)^2 \quad (1)$$

Where $\Phi_{unk}$ is i the fluorescence quantum yield of the sample, $\Phi_{std}$ is the fluorescence quantum yield of the standard, $I_{unk}$ and $I_{std}$ are the integrated emission intensities of the sample and the standard, respectively, $A_{unk}$ and $A_{std}$ are the absorbance of the sample and the standard at the excitation wavelength, respectively, and $n_{unk}$ and $n_{std}$ are the refractive indexes of the corresponding solution.

General Procedure for the SDS-PAGE and Gel Image

The electrophoresis experiment was carried out on a polyacrylamide mini-gel (1 mm thick) using a discontinuous buffer system. The stacking gel contained 10% polyacrylamide in a 0.4 M borax-boric acid buffer solution (pH 8.7), and the separating gel contained 5% polyacrylamide in a 0.12M Tris-HCl buffer solution (pH 6.8). The running buffer contained 20 mM borax-boric acid, pH 8.7, 0.1% (w/v) SDS in water. All solutions were freshly prepared prior to use. SDS-PAGE was carried out on a vertical polyacrylamide gel system until the protein bands reach the interface of the separating gel. Separation was performed at a constant voltage of 105 V. The instrumental setup consisted of an electrophoresis chamber (model DYCP-31DN) connected to a DYY-8C electrophoresis power supply, both from Beijing Liuyi Electrophoresis. The electropherograms were obtained on a Tanon GIS 2010 (Shanghai Tanon Sci. & Tec. Co., Ltd.) gel image system and the data were analyzed by Tanon image analysis software. General staining procedure: Compound 1c was dissolved in AcOH:MeOH:$H_2O$=3:10:87 v/v at a concentration of 0.5 mg/mL with 0.5% (wt %) SDS. Bromophenol Blue which added to the protein as indicator was washed off firstly, the color changed from blue to shallow yellow after 2 h. The protein gels were stained with the solution of 1c for 2 h and images can be obtained using image analysis system. Then the excess 1c was removed from the gels by immerging the gels into the dye eluent, scanned using the image analysis system after 4 h.

Atomic Force Microscopy (AFM)

Samples for the imaging were prepared by spin casting the squaraine dye solution (in $H_2O$ containing 0.05% wt SDS) in the absence and presence of BSA at the specified concentration. AFM images were recorded under ambient conditions using a Park Scientific Autoprobe CP, which is operating in the tapping mode with Micromasch tapping probes with radius of curvature being <4 nm. The tips were brand new.

Synthesis and Characterization

The squaraine (SQ) dyes 1a-c are synthesized by using a modified procedure reported by Santos, et al. (cited above). $^1$H NMR of 1b exhibits two vinyl signals at 6.55 and 6.18 ppm (1:1 ratio) (FIG. 2), in contrast to one vinyl signal from 1c at 6.0 ppm. Observation of two vinyl protons in 1b, as well as two non-equivalent ethyl groups, indicates that the amino nitrogen has a strong interaction with the carbonyl group on the four membered squaraine ring. The N—H proton of 1b in $CDCl_3$ occurs at 9.137 ppm as a broad peak (inset (a), curve C). Further examination of the $^1$H NMR spectrum of 1b at diluted concentration shows that the resonance signal of N—H proton is slightly shifted downfield to 9.165 ppm (curve A). The trend suggests that the intermolecular hydrogen-bonding is not likely to occur for 1b, as weakening of the hydrogen-bonding by decreasing concentration would typically shifts the signal upfield. In the DMSO-$d_6$ solvent, the N—H signal of 1b is shown as a relative sharp triplet (δ=9.41 ppm, j=6.3 Hz) (FIG. 2, inset (b)). In addition to the narrow signal, observation of the clear coupling between N—H and adjacent —$CH_2$ further supports the assumption that the N—H proton is reluctant to participate in the H-bonding with the nearby hydrogen bond acceptors such as DMSO.

Figure 3:
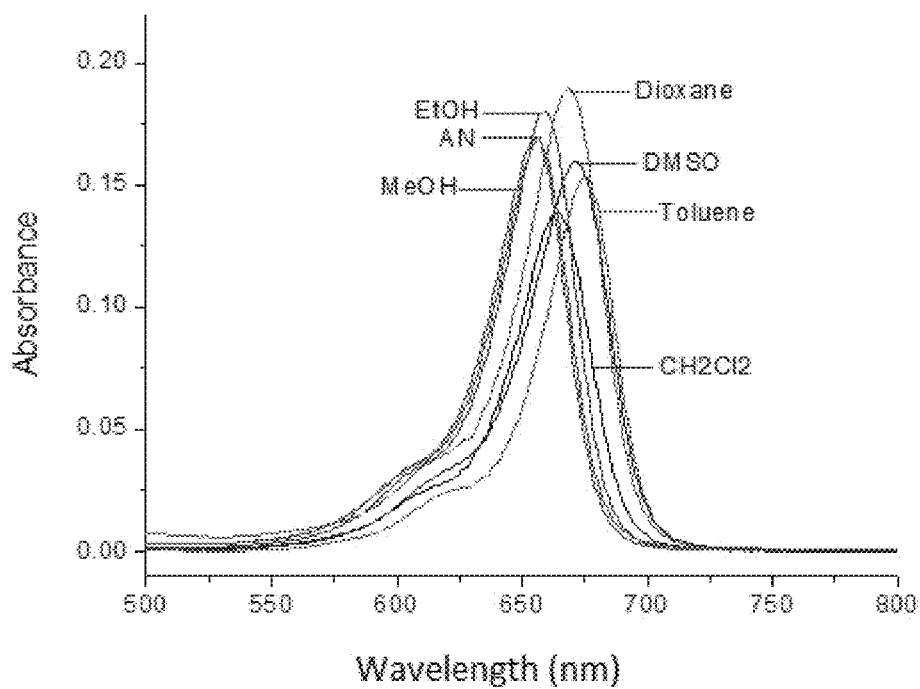
FIG. 3 shows the absorption spectra of 1b (5 μM) in different solvents.
Figure 4:
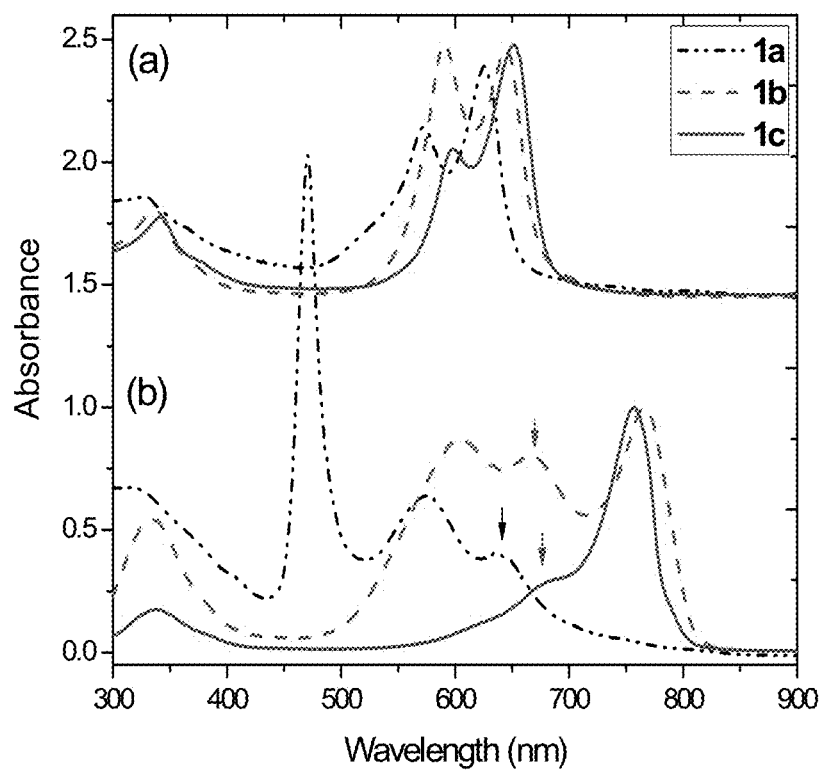
FIG. 4 shows UV-vis absorption spectra of 1a-1c in water (5 μM) in the absence (top, (a)) and presence (bottom, (b)) of 0.05% SDS, with the arrows in the bottom panel indicating the corresponding monomeric species.

UV-vis absorption spectra of 1b in various organic solvents shows one band at about 670 nm with similar absorbance, attributing to the monomeric form (FIG. 3). Solvent polarity only slightly affects the absorption peak, with $\lambda_{max}$=676 nm in the nonpolar toluene and $\lambda_{max}$=656 nm in methanol for 1b. Interestingly, absorption spectrum of 1b in aqueous solution displays an additional peak that is about 50 nm blue-shifted from the monomer band (e.g. $\lambda_{max}$=591 and 644 nm for 1b), as a consequence of decreased solubility (FIG. 4a). The new band at 591 nm can be assigned to H-aggregate on the basis of the observed spectral shift. The relative absorption intensity of the new bands falls in the order: 1b>1a>1c, reflecting their relative tendency in forming the respective aggregate in aqueous solution. Addition of the anionic surfactant (sodium dodecyl sulfate, SDS) (1.7 mM or 0.05% wt), however, leads to strikingly different spectra (FIG. 4b). For 1b and 1c, the new bands occur at longer wavelength ($\lambda_{max}$=767 and 757 nm, respectively), which are assigned to J-aggregate. In sharp contrast, the new band for 1a occurs at a much shorter wavelength ($\lambda_{max}$=470 nm), whose narrow band characteristics suggests a well defined structure. This high energy absorption band is attributed to H-aggregate, since it is blue-shifted from the monomer absorption and not detected in other solvent systems. The finding clearly reveals that the interaction of SDS with the positive charge-bearing dyes 1 disrupts the noncovalent interactions between the dye molecules and promotes the J-aggregation for 1c and H-aggregation for 1a. Since the concentration of SDS is below its critical micelle concentration (CMC=0.0082 M in pure water at 25° C.), the surfactant molecules are expected to be in the single molecular form (not aggregate). It is possible that the anionic end of the surfactant interacts with the cationic site of 1, thereby making the squaraine dye less polar to promote the aggregation in aqueous solution. The reasons for the intriguing H- and J-aggregation selectivity are not fully understood.

Aggregation Structure

Figure 5:
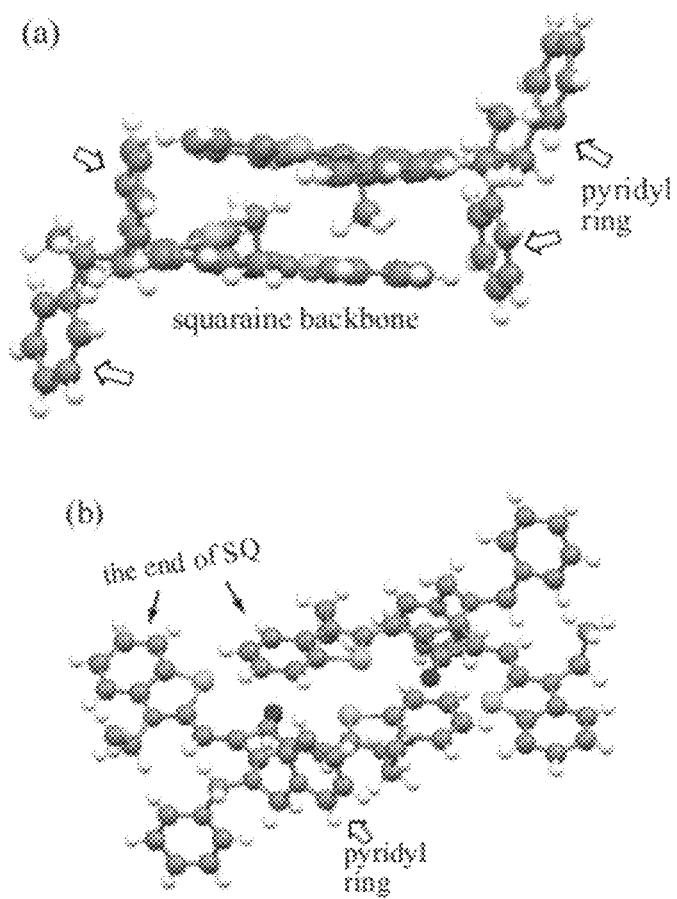
FIG. 5 shows the crystal packing of the squaraine dye 1c, wherein, in (a): two pyridyl groups are pointing toward opposite directions of the conjugated plane, and, in (b): the tilted structure shows that one end of a first dye 1c is aligned with the four-membered ring of another dye 1c to give a J-aggregate assembly.

The steric bulkiness of the R group in 1 could play an important role in the H- or J-aggregation selectivity. On the basis of the crystal structural data, both sulfur atoms in 1 are on the same side as the oxygen of the four membered ring. The two pyridyl groups in 1c are pointing to the opposite direction of the squaraine plane. Crystal packing of 1c further reveals that the squaraines are arranged in a manner similar to J-aggregate, in which the interacting squaraines only overlap partially (i.e., one end of the SQ aligned with the four-membered ring of the other SQ) (FIG. 5b). It can be assumed that the J-aggregate formed from 1c in the aqueous solution adopts the similar arrangement.

Figure 2:
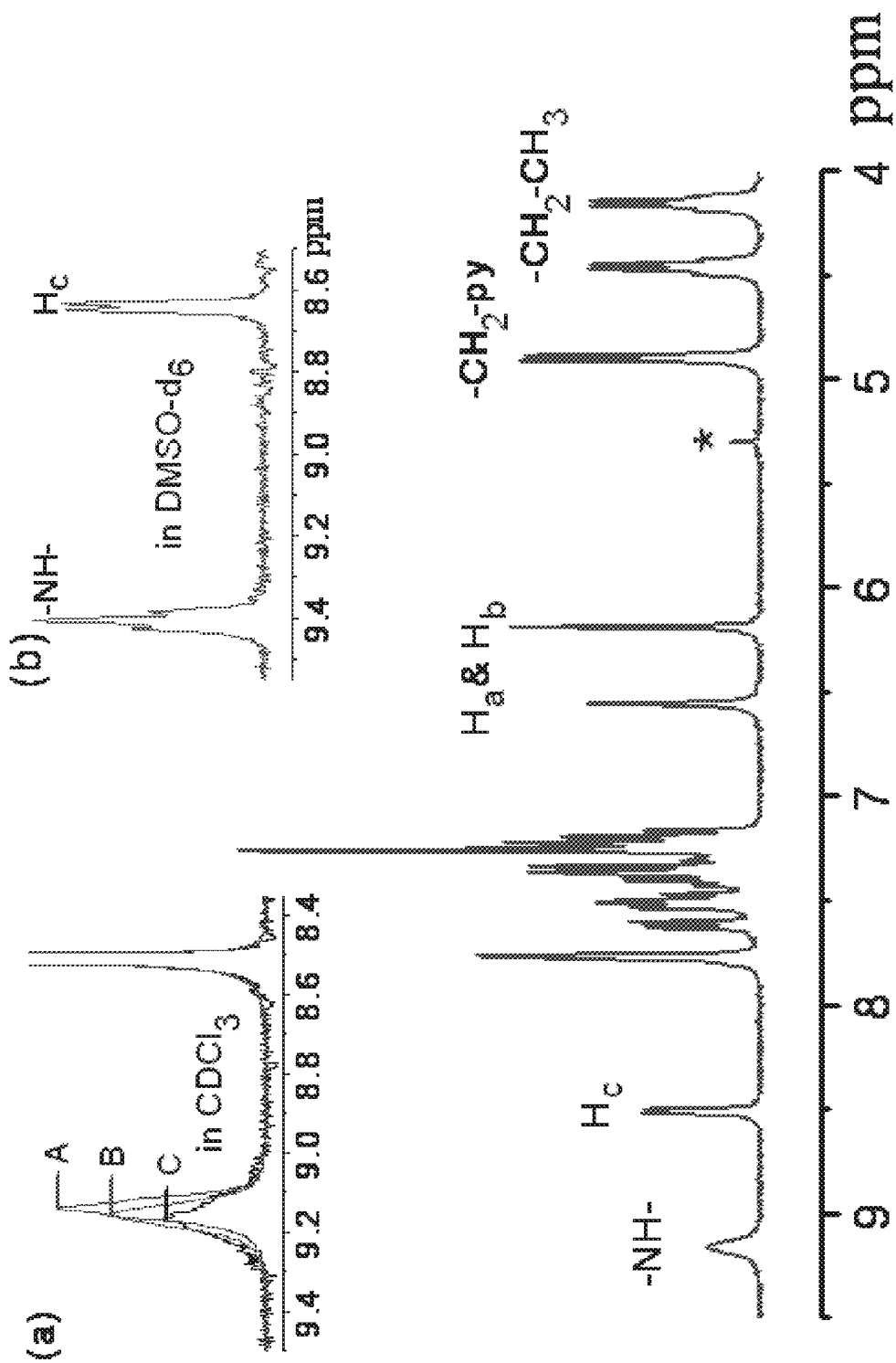
FIG. 2 shows the $^1$HNMR spectrum of squaraine dye 1b in $CDCl_3$, where the asterisks at 7.2 and 5.3 ppm are attributed to $CHCl_3$ and $CH_2Cl_2$ residue, respectively; the inset (a) shows the spectra of 1b at different concentrations in $CDCl_3$ (solution concentration in the order: curve A>B>C); and the inset (b) shows the spectrum of 1b in DMSO-$d_6$.
Figure 6:
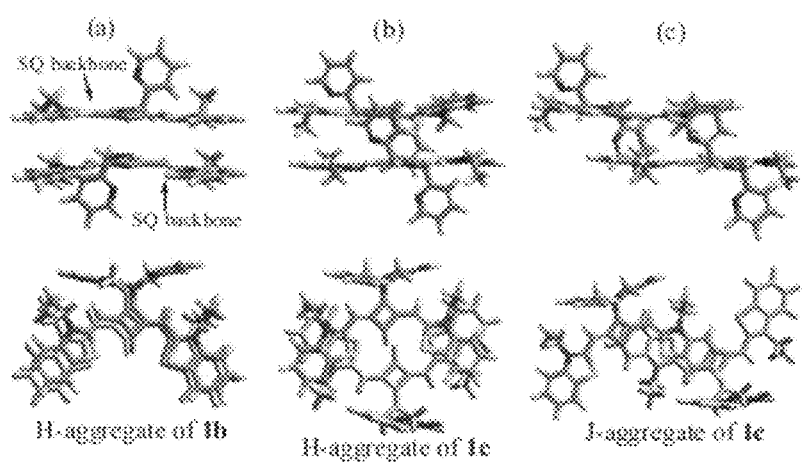
FIG. 6 shows molecular modeling of 1b in H-aggregation (a), and 1c in H-aggregation (b) and J-aggregation (c), which are viewed from the side (top row) and top (bottom row), respectively.
Figure 7:
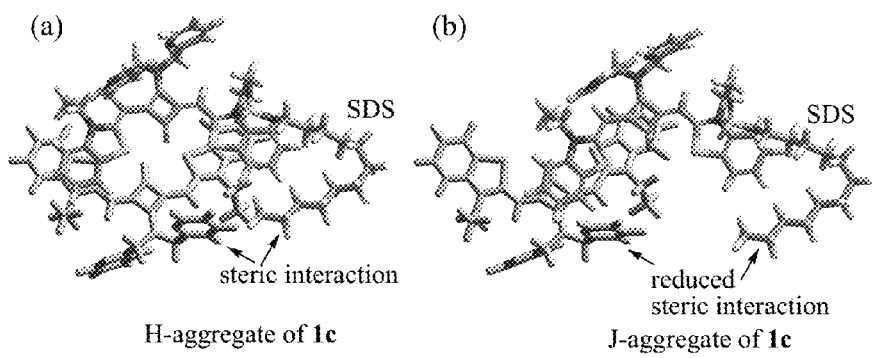
FIG. 7 is a schematic illustration of interaction between the aggregate of 1c and SDS, exhibiting that the steric interaction between the SDS chain and pyridyl ring on SQ backbone disfavors the H-aggregte (a), leading to formation of J-aggregate (b)

The molecular arrangements in H- or J-aggregate are further examined by using the molecular modeling (FIG. 6). It should be noted that the H-aggregate formation requires the interacting chromophores to be parallal in close proximity, which is more sensitive to the steric hinderance at the center of the chromophore (in comparison with J-aggregate). The squaraine 1b (R=—NH—$CH_2$-py; py=pyridyl group) can adopt a parallel H-aggregate form (FIG. 6a), in which the two molecules have a maximum π-π it interaction. Due to increased steric bulkiness (R=—N—($CH_2$-py)$_2$), the two squaraine planes of 1c in the H-aggregate are likely to have the anti-parallel arrangement (FIG. 6b), which is energetically less favorable because of the smaller overlap of conjugated backbones (smaller π-π it interaction). In other words, squaraine 1c has the least tendency to exhibit H-aggregate in aqueous solution (FIG. 4a), and has a higher tendency to form J-aggregate. For the molecule 1a, the smaller substituent (R=—$OCH_3$) increases its tendency to form parallel H-aggregate. In addition to the steric reasons, the impact for H- and J-aggregate formation appears to be dramatically enhanced by the addition of a small amount of SDS (FIG. 4b), with 1a giving primarily H-aggregate while 1c forming mainly J-aggregate. The moderate steric bulkiness of —NH—$CH_2$-py in 1b, could be responsible for the formation of both H- and J-aggregate. The role of possible hydrogen-bonding with water molecules and SDS might be a less important factor for 1b as indicated in the previous discussion (FIG. 2). The influenece of the added SDS can be rationalized by considering the steric interaction between the incoming SDS and squaraines. Under dilute condition used, the alkyl chain of SDS in aqueous is likely to adopt a fold conformation in some degree to minimize its interaction with surrounding polar water molecules. When the SDS approaches 1c in H-aggregate, the freely mobile alkyl chain could have some steric interaction with the pyridyl (as shown in FIG. 7a). This factor perturbs the H-aggregate structure to lead to energetically more favorable J-aggregate, in which the pyridyl group is moved away from the SDS molecule (indicated by arrows in FIG. 7b). In the squaraine 1a, such steric interaction with SDS is absent, and the association of SDS with 1a reduces the solubility and promotes the H-aggregation of 1a.

Absorption and Fluorescence Response to BSA

Figure 8A:
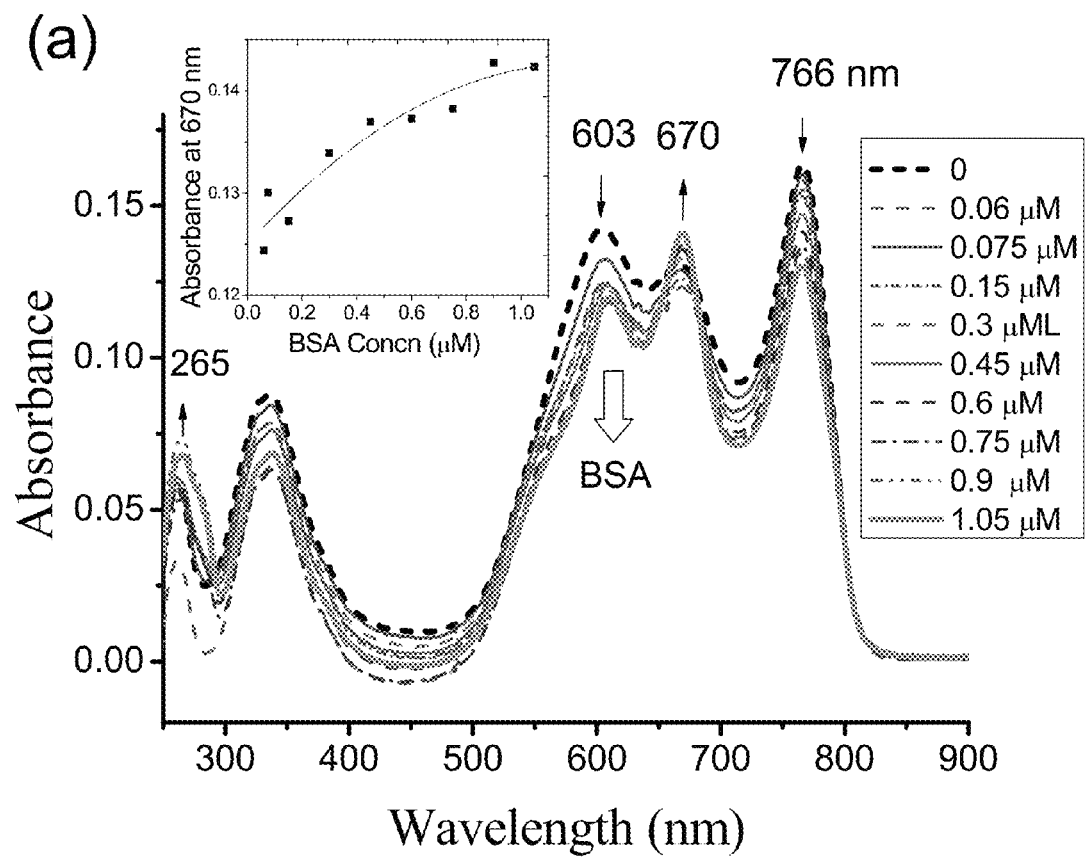
FIG. 8(a) shows the absorption spectra of squaraine 1b (5 μM), the inset shows the absorbance response to protein concentration.
Figure 8B:
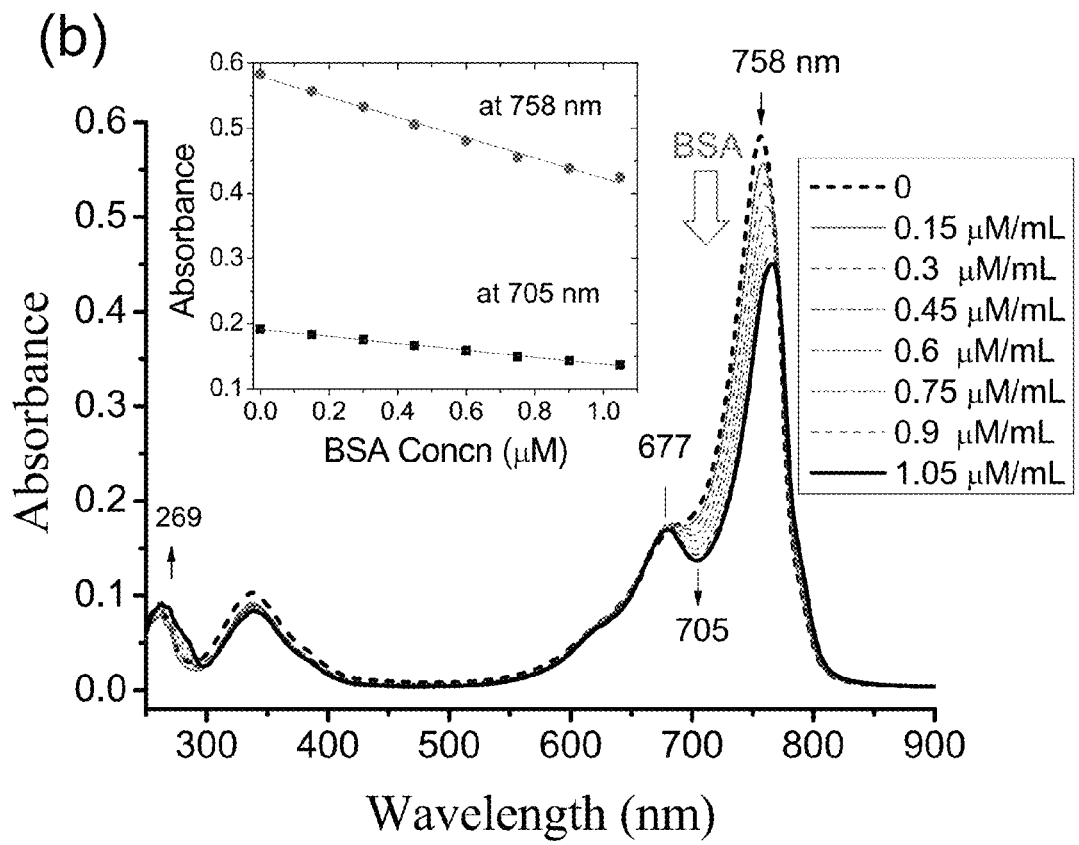
FIG. 8(b) shows the absorption spectra of squaraine 1c (5 μM), the inset shows the absorbance response to protein concentration.

Absorption spectrum of 1b in water reveals three peaks at 603, 670 and 766 nm (FIG. 8a), which can be attributed to H-aggregate, monomer and J-aggregate, respectively, on the basis of the observed spectral shift. Addition of BSA to the solution decreases the aggregation absorption bands at 603 and 766 nm, while the monomeric absorption band at 670 is notably increased. The result indicates that the BSA favors to interact with squaraine dye in the monomeric form. The same trend is also observed in the response of 1c to BSA. Upon addition of BSA, the J-aggregate, which is observed as the predominant peak at $\lambda_{max}$=758 nm in the UV-vis spectrum of 1c (FIG. 8b), gradually decreases along with increasing content for the monomeric species (minor peak at $\lambda_{max}$=677 nm). Addition of the protein also caused the absorbance increasing at ≈270 nm, which corresponds to the tryptophan chromophore in BSA, suggesting that the interaction between squaraines and tryptophan chromophore located at site I of BSA, mainly involving π-stacking and hydrophobic interaction. Analysis of absorbance data gave a 1:1 stoichiometry for the complexes between squaraine dyes and BSA. The binding constants were calculated to be $5.0 \times 10^5$ $M^{-1}$, $1.5 \times 10^6$ $M^{-1}$ and $8.5 \times 10^5$ $M^{-1}$ for 1a, 1b and 1c, respectively.

Figure 9:
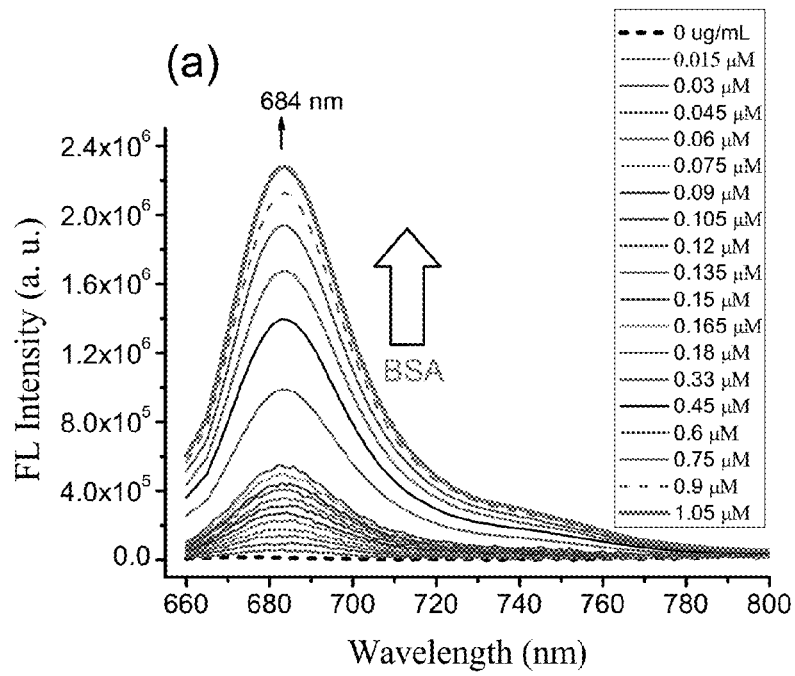
FIG. 9 shows the fluorescence spectra of squaraine 1b (5 μM) with different concentration of BSA in water containing 0.05% SDS (excitation at 640 nm)

Compound 1 exhibits weak fluorescence in aqueous solution (1a: $\phi_{fl}$=5.8×10$^{-3}$; 1b: $\phi_{fl}$=0.023; 1c: $\phi_{fl}$=0.010), due to its high tendency to form aggregates. In the presence of the anionic surfactant (sodium dodecyl sulfate, SDS) (1.7 mM or 0.05% wt), the fluorescence signals are further decreased by a factor of about 3. Interestingly, the fluorescent intensity ($\lambda$em at ~690 nm) increases significantly upon addition of BSA (FIG. 9). Although the J-aggregates have strong absorption at ~760 nm, no fluorescence signals are detected near this wavelength, indicating that the J-aggregate from 1 is non-emissive. The emission signals at ~684 nm is assigned to the monomeric 1b, as the fluorescence of squaraine dye typically has a small Stokes' shift (about 10-30 nm). The protein-induced fluorescence is visible by naked eye, when a beam of a common red laser pointer is passed through the solution (as schematically shown in FIG. 1). Similar fluorescence enhancement is also observed from 1a and 1c after the addition of BSA. In the presence of 70 mg/mL BSA and 0.05% SDS in aqueous, the quantum yields are determined to be $\phi_{fl}$=0.055 for the 1a+BSA, $\phi_{fl}$=0.31 for 1b+BSA, and $\phi_{fl}$=0.22 for 1c+BSA.

Figure 10:
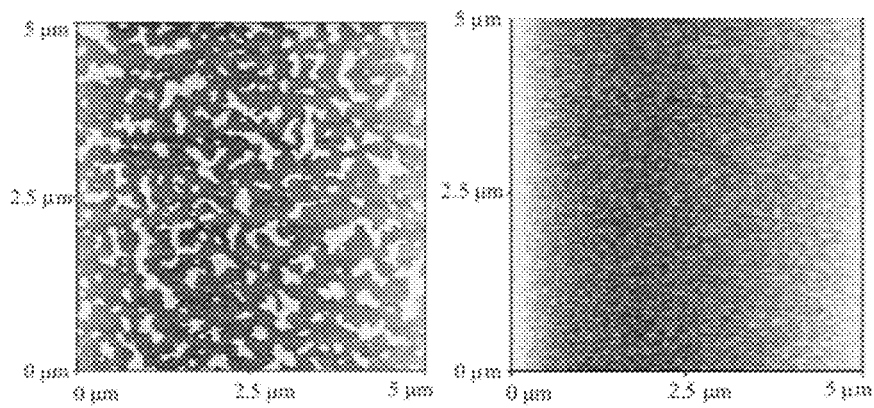
FIG. 10 shows atomic force microscopy images of squaraine 1c (left), and BSA+1c (right) containing SDS (0.05% wt in $H_2O$), wherein the solution concentrations used for film preparation were 10 μM for the squaraine dye, and 23 μg/mL (1.05 μM) for BSA.

The intriguing BSA-induced fluorescence turn-on is attributed, at least in part, to the dissociation of squaraine aggregates (which are non-fluorescent), as it is evident from the UV-vis absorption spectra (FIG. 8). Atomic force microscopy (AMF) (FIG. 10) further confirms that the interaction with BSA strongly affects the aggregate. The aggregates of 1 are estimated to be in the range of 0.1-0.5 μm (or 100-500 nm), which completely disappears in the presence of BSA (the size of the SQ-BSA complex is only about 20 nm). The results clearly point to that the fluorescence turn-on is due to the structural changes of aggregation, resulting from its interaction with proteins.

Figure 11:
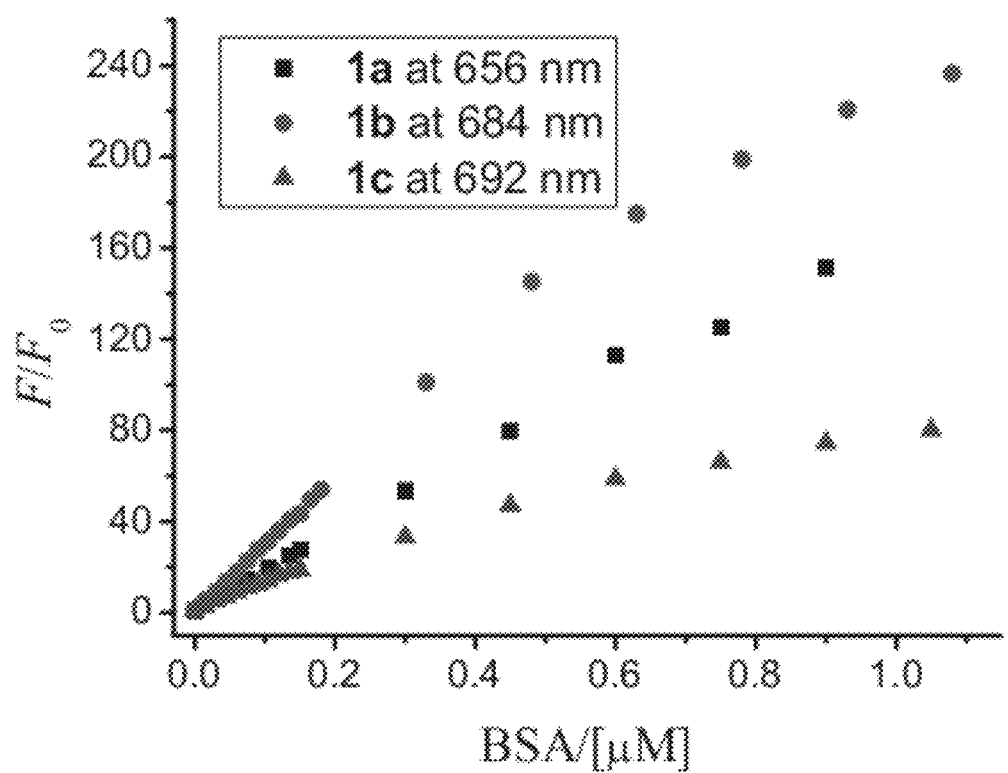
FIG. 11 shows a graph of the fluorescence intensity of squaraines 1a, 1b and 1c as a function of BSA concentration, using fluorescence intensities at the respective wavelengths indicated in the inset.

The fluorescence enhancement is dependent on the number of dye molecules which migrates from the aggregate states to the BSA binding sites (as non-aggregate). In responding to the BSA concentration, the fluorescence intensities of 1a-1c exhibit good linear correlation over a wide concentration range (up to ~0.45 μM) (FIG. 11). The fluorescence of 1b is constantly higher than that of 1a and 1c in the BSA concentrations investigated, suggesting that the H-aggregates (poor emitter) of 1b also plays a positive role in the observed fluorescence turn-on. As seen from FIG. 8a, the squaraines of 1b in both H- and J-aggregates are consumed about equally to interact with BSA. Higher fluorescence enhancement from 1a than that from 1c further suggests that the H-aggregate could contribute more to the enhancement than the J-aggregate. The assumption is consistent with the observation that the fluorescence enhancement from 1b is approximately the sum of that from 1a (primarily H-aggregate) and 1c (primarily J-aggrgate). The fluorescence enhancement upon binding BSA reaches over 200-fold, which is quite large in comparison to other reported dyes that undergo protein-induced fluorescence. The detection limit is 800 ng/mL of BSA (signal-to-noise ratio was 3).

Large fluorescence turn-on (~200 fold), associated with the low conversion of aggregate to monomeric species (FIG. 8), suggests that the other factors are involved. Absorption spectra reveals that the squaraines 1a-c exist nearly exclusively in the monomeric form in ethanol, attributed to its improved solubility. The fluorescence of the monomeric 1a-c is found to be increased significantly by addition of glycerol, a viscous solvent which is known to slow down the non-radiative decay rate ($k_{nr}$) of fluorescent molecules. The result indicates that the fluorescence of the monomeric 1a-c can be significantly enhanced by changing the molecular environments. Therefore, it is likely that a tight binding to the protein environment, possibly at the hydrophobic pockets, increases the molecular rigidity of 1, which reduces the vibrational modes and further raises the fluorescence signal.

The fluorescence response of 1a-c to other proteins in aqueous solution in the presence of SDS (1.7 mM) were also investigated, and the results are summarized in Table 1. The response to BSA is normalized to 1.00. For other proteins, lysozyme, trypsin, formaldehyde dehydrogenase and thrombin, the protein-to-BSA ratios are less than 0.52, showing that these squaraine dyes exhibit some selectivity in responding to BSA. The observed selectivity can be attributed to the electrostatic interaction, because BSA is a negatively charged amphiphilic macromolecules, which facilitates its interaction with the oppositely charged squaraine dyes. In addition, BSA has hydrophobic pockets in its structure. These interactions serve as driving forces to transfer the dye molecules from their non-emissive aggregate states to the fluorescent monomeric form (via complexation with BSA). Lower response toward other proteins is presumably related to their different hydrophobic character, which is determined by the hydrophobicity of the consituent amino acids and the suitable hydrophobic "cleft" associated with the three-dimensional protein structures.

TABLE 1

Protein-to-protein variation of 1a-c

| Proteins | 1a | 2b | 2c |
|---|---|---|---|
| | | Protein vs BSA | |
| BSA | 1.00 | 1.00 | 1.00 |
| Lysozyme | 0.14 | 0.37 | 0.19 |
| Trypsin | 0.34 | 0.31 | 0.35 |
| Formaldehyde Dehydrogenase | 0.52 | 0.39 | 0.52 |
| Thrombin | 0.06 | 0.03 | 0.19 |

The response of 1c to selective inorganic salts and reductants was examined to evaluate the interference. All the test were carried out by using 5 μM 1c with one equivalent of BSA and 0.05 wt % SDS, in the presence of an excess amount of foreign substances. The maximum concentrations which perturb the fluorescence intensity by less than 10% are 1.0 mM for $KNO_3$, 0.02 mM for $ZnCl_2$ and $CaCl_2$, 0.1 mM for cyateine and 0.02 mM for gluthione.

To illustrate the application of the BSA fluorescent indicator, BSA after electrophoresis using SDS-PAGE minigels were stained by 1c and were scanned using image analysis systems. The images would not print adequately through the publication processes afforded this present disclosure and so are not included here. However, spots on the gels show that the squaraine dye 1c is sensitive for BSA sensing. A protein spot at 10 μg BSA after washing exhibited only slightly stronger fluorescence intensity than that at 2 μg. In comparison to the method of protein labeling reaction, reported by Wang, et al. *J. Org. Chem.* 2009, 74, 7675-7683, squaraine dyes provide the noncovalent and special BSA sensing to avoid fussy and troublesome succinimidyl ester activated reaction of dyes before staining. Squaraine dyes have shown the potential to have great value as a new kind of fluorogenic sensor that noncovalently binds to BSA.

In summary, we have demonstrated that squaraine dyes 1a-1c have high tendency to form non-fluorescent H- and/or J-aggregates in aqueous solutions. With the aid of anionic surfactant, the squaraine dyes can exist in primarily H-aggregate (for 1a) or J-aggregate (for 1c) forms. Through noncovalent interaction with the biomacromolecules, these squaraine dyes exhibit large fluorescence response to proteins. The proposed fluorescence turn-on mechanism is based on the transformation of the dye molecules in aggregate states, which are non-fluorescent, to the fluorescent state upon protein binding. The H-aggregate appears to contribute more to the fluorescence enhancement. The rigid environment, achieved by strong complexation with protein, is also believed to play an important role in the observed large fluorescence turn-on. The mechanism is consistent with the reasoning that the binding sites of proteins, which are located within the protein structure, favor the squaraines in the monomeric rather than the more bulky aggregate forms on the basis of protein hydrophobicity. The new squaraine probes have the following advantages: (1) large fluorescence enhancement, reaching more than 200-fold upon binding BSA; (2) fluorescence response in the NIR region ($\lambda$em≈690 nm); and (3) selective response to BSA over other proteins with low hydrophobic character.

Experimental Results for Compositions of SQ Dyes and Graphene

Figure 12A:
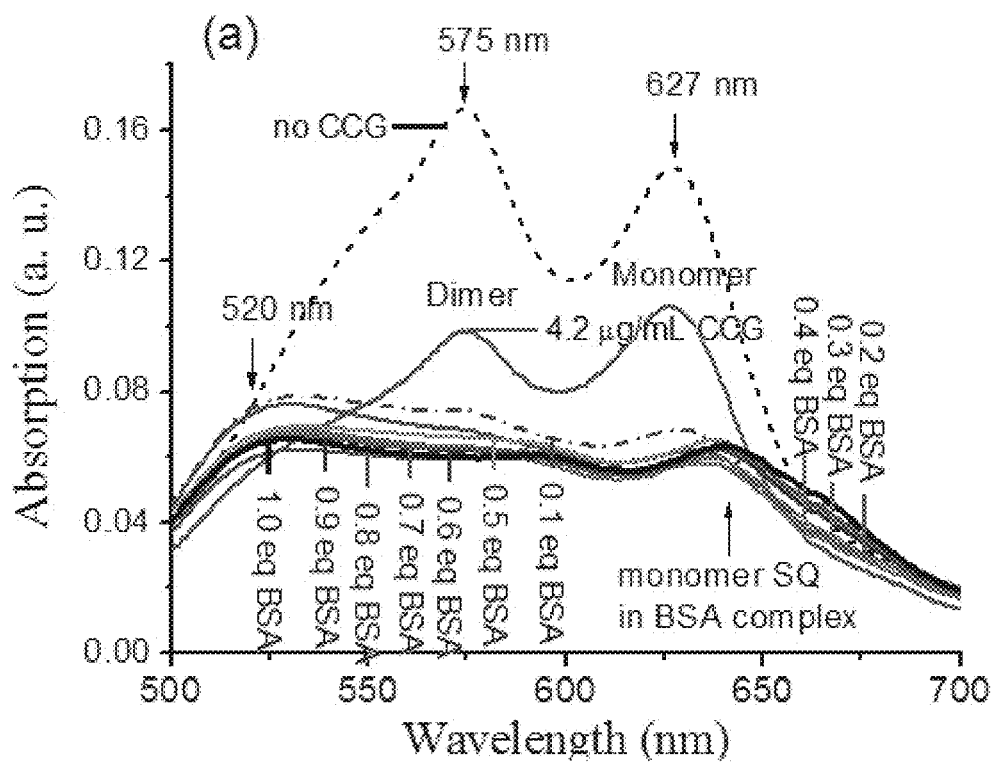
FIG. 12(a) shows absorption change of 1a (5 μM) in aqueous solution upon addition of BSA in the presence of 4.2 μg/mL chemically converted graphene (CCG)
Figure 12B:
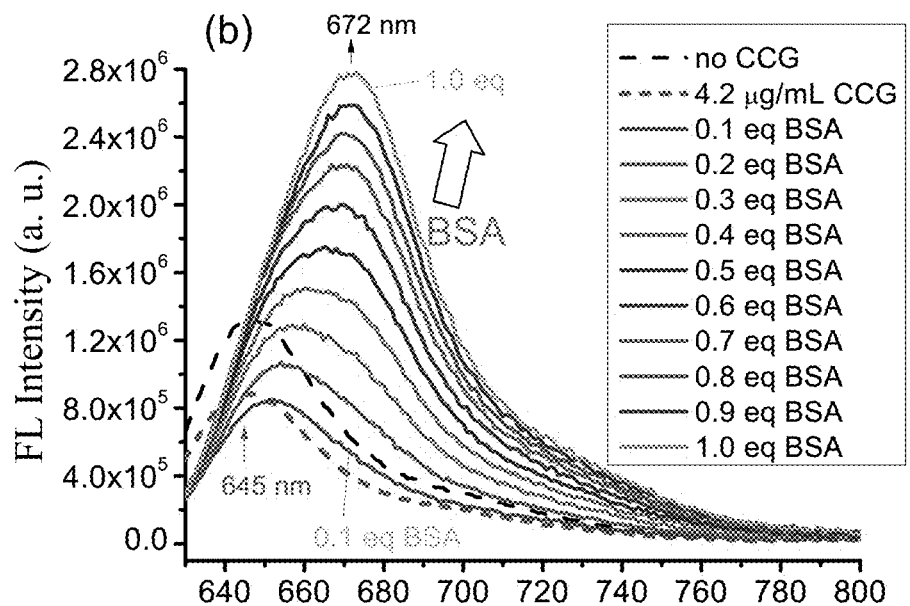
FIG. 12(b) shows fluorescence change of 1a (5 μM) in aqueous solution upon addition of BSA in the presence of 4.2 μg/mL CCG.

Graphene oxide (GO) and chemically converted graphene (CCG) were prepared using the Hummers method, followed by reduction with hydrazine hydrate. UV-Vis of SQ in aqueous solution revealed two absorption bands ($\lambda$max≈625 & 575 nm), attributable to the monomer and hypsochromic dimer absorption, respectively (FIG. 12). The monomer and dimer absorption gradually disappeared, when the CCG concentration in aqueous solution was increased. Observation of a new band at about 520 nm indicated that the SQ molecules were transformed to H-aggregates. Upon addition of CCG, the fluorescence of the dye molecule was quenched, presumably due to the strong photoinduced electron or energy transfer between SQ and CCG as reported for pyrene and GO. The spectral response clearly indicated strong electrostatic and π-π interactions between SQ and CCG.

Addition of BSA into SQ-CCG solution revealed little impact on the absorption (FIG. 12(*a*)). Interestingly, the fluorescence intensity of the solution was remarkably increased (FIG. 12(*b*)), while the emission peak was red-shifted by about 30 nm to 670 nm. Similar responses were also observed from SQ 1b and 1c. Control experiments showed that 1a exhibited weak response to BSA without CCG, and 1b and 1c exhibited essentially no fluorescence response to BSA in the absence of CCG, indicating that CCG was necessary to achieve the large fluorescence response.

Figure 13A:
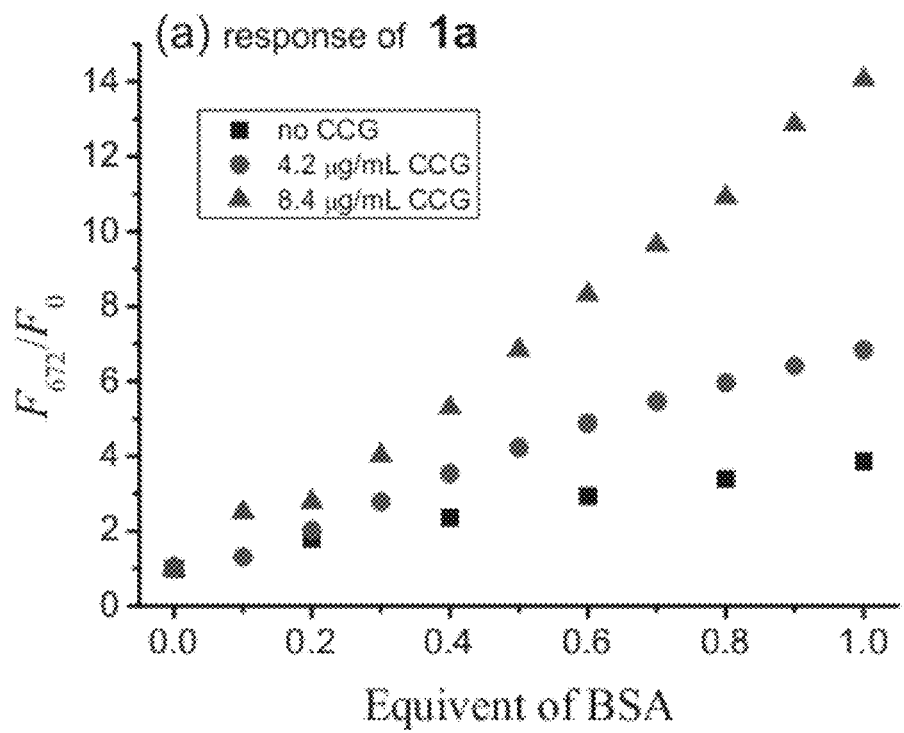
FIGS. 13(a) and (b) show the fluorescence response of 5 μM of 1a (FIG. 13(a)) and 5 μM of 1b (FIG. 13(b)) at the emission peak wavelength (672 nm for 1a, 678 nm for 1b) upon addition of different equivalent of BSA in aqueous solution in the presence of various concentration of CCG.
Figure 13B:
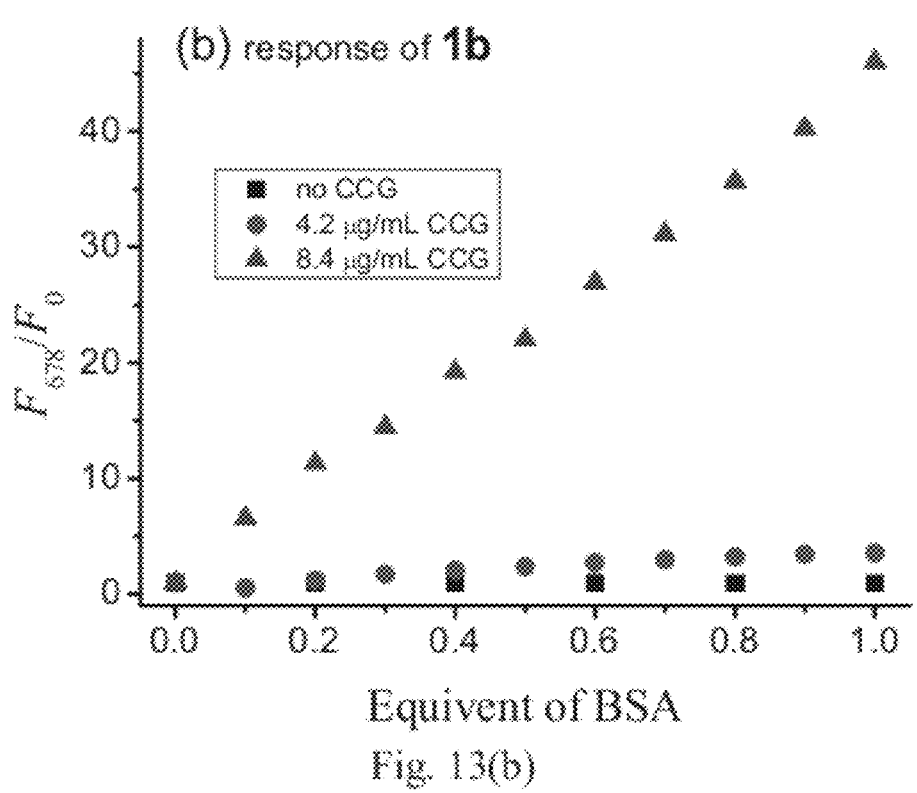

The magnitude of the fluorescence enhancement was associated with the ratio of SQ to CCG used. Using 8.4 μg/mL of CCG solution was found to give the optimum result (FIGS. 13(*a*) and (*b*)). The fluorescence response exhibited a good linear correlation to BSA, indicating its analytical value. Interestingly, the release of SQ dyes from SQ/CCG complexes appeared to be dependent on the proteins. For example, one equiv of BSA increased the fluorescence intensity of 1b ($F_{678}/F_0$) by a factor of 46 (FIG. 13(*b*)), while one equiv of lysozyme caused negligible response under the same condition.

Addition of BSA raised the fluorescence signals, with the emission being red-shifted by about 20 nm to ~675 nm. The fluorescence enhancement for 1b reached to as high as 80 fold at 678 nm, in contrast to 27 fold (for 1a) and 8 fold (for 1c). Clearly the system benefited from using graphene (FIG. 14), which forms a complex with SQ causing a decrease in fluorescence. Interaction with BSA gave the large fluorescence turn-on, accompanied with a gradual emission redshift (when BSA <0.6 eq, see FIG. 12). The spectral response was associated with gradual entrance of SQ dye into the cavity within BSA, which provides a rigid and hydrophobic environment to enhance the fluorescence and to cause spectral red shift.

Figure 15:
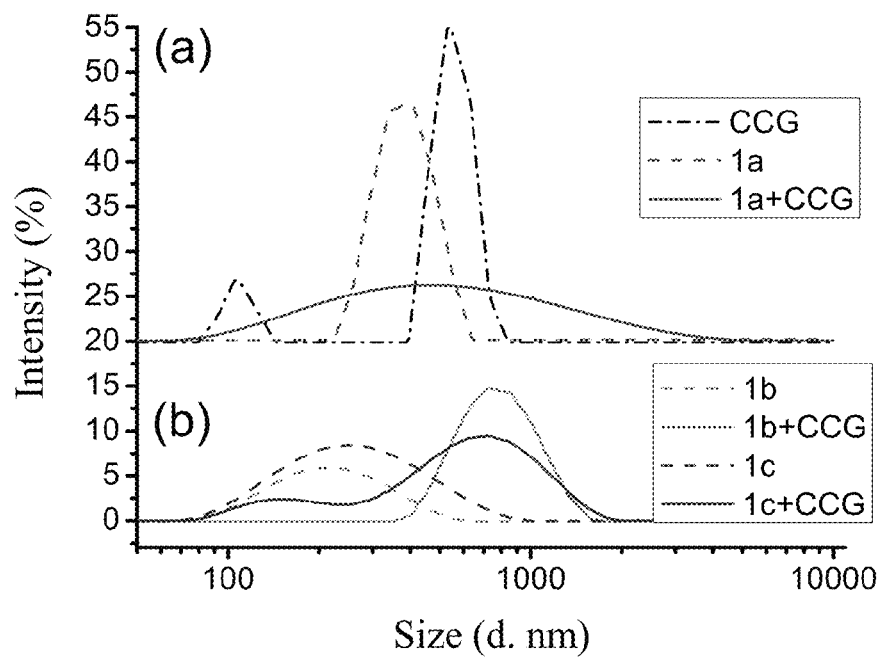
FIG. 15 shows the solvodynamic diameters of CCG, SQ 1a-c and CCG+1a-c (solid line) in water determined by dynamic light scattering.

Dynamic light scattering (DLS) techniques were employed to probe the size and the self-assembly structures in solutions. Upon mixing, the relatively sharp peaks for 1 and CCG merged into a broader peak with a notable particle size increase (FIG. 15), supporting the assumption that the assembly of SQ molecules on the CCG sheets occurred in solution.

To further evaluate the variation in size associated with the molecular interaction, the surface morphology of CCG and SQ-CCG was analyzed by using tapping mode atomic force microscopy (AFM). In the absence of SQ dyes, the height of CCG was in the range of ~0.7 nm. Upon complexation with SQ dyes, the height was increased to 7-8 nm (average about 7.3 nm). Observation of the increased thickness supported the assumption that the SQ dyes were assembled on the graphene surface as aggregates. From the x-ray data of 1b and 1c, the distance between the two parallel SQ molecular planes is about 0.37 nm. One can assume that the molecular packing distance remains to be similar in the aggregate states. Significant height increase on the SQ-CCG surface was in favor of the H-aggregates, which was consistent with the absorption spectra. It should be pointed out that the estimated H-aggregate thickness was based on the assumption that the species observed in AFM was a single piece of CCG-SQ.

Since the positive charge on the SQ is partially neutralized by complexation with CCG, the SQ dyes in the CCG/SQ complex would be more hydrophobic than the free SQ. This favorable hydrophobic characteristic could influence the delivery of the SQ dyes to BSA. To understand the site-selective binding of CCG/SQ complex with BSA, we employed ligand displacement using known site selective binding ligands, such as dansylamide (DNSA, for site I) and dansylproline (DP, for site II). Addition of DP or DNSA to a solution of the BSA-CCG/SQ complex resulted in gradual decrease of fluorescence intensity, indicating that an effective displacement of SQ from BSA by the binding ligands. Plot of fluorescence response to the added ligands revealed that the SQ dyes were binding to both site I and II of BSA with preference to site I.

When the protein lysozyme of low hydrophobic character was used instead of BSA, no obvious fluorescence turn-on was observed under the same conditions. The result further corroborated that the binding affinity with protein was mainly driven by hydrophobic interaction.

Figure 14:
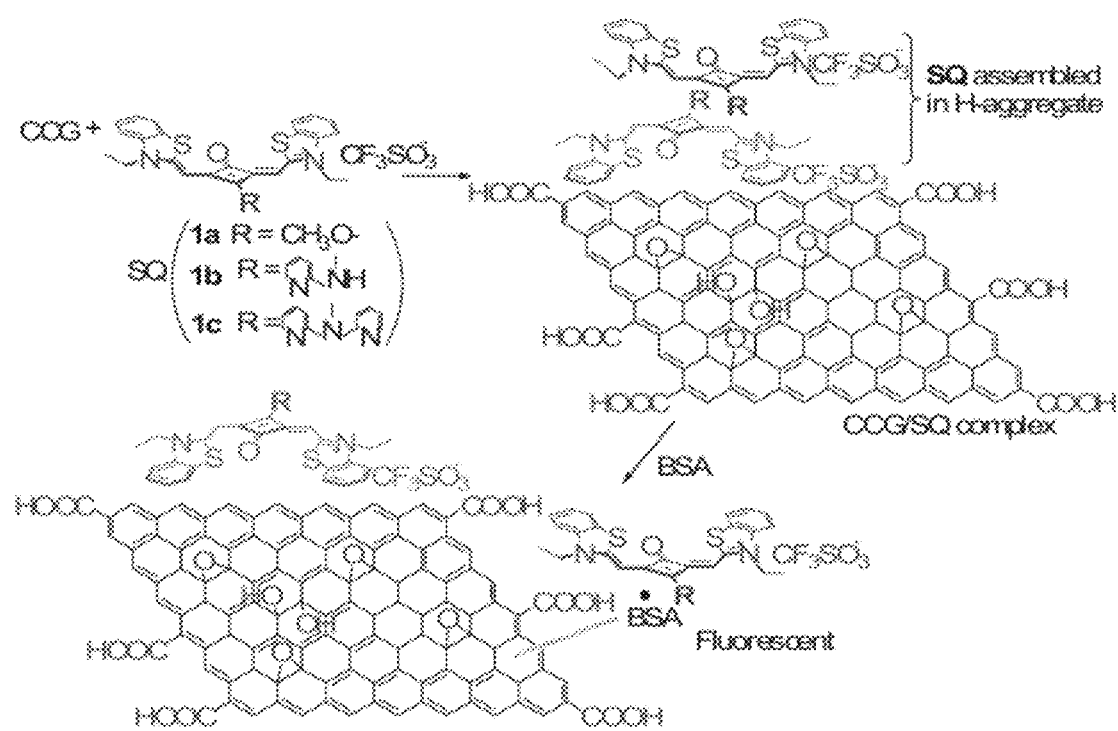
FIG. 14 is a hypothetical illustration of the assembly formed by squaraine dye in the presence of CCG and BSA.
Figure 16:
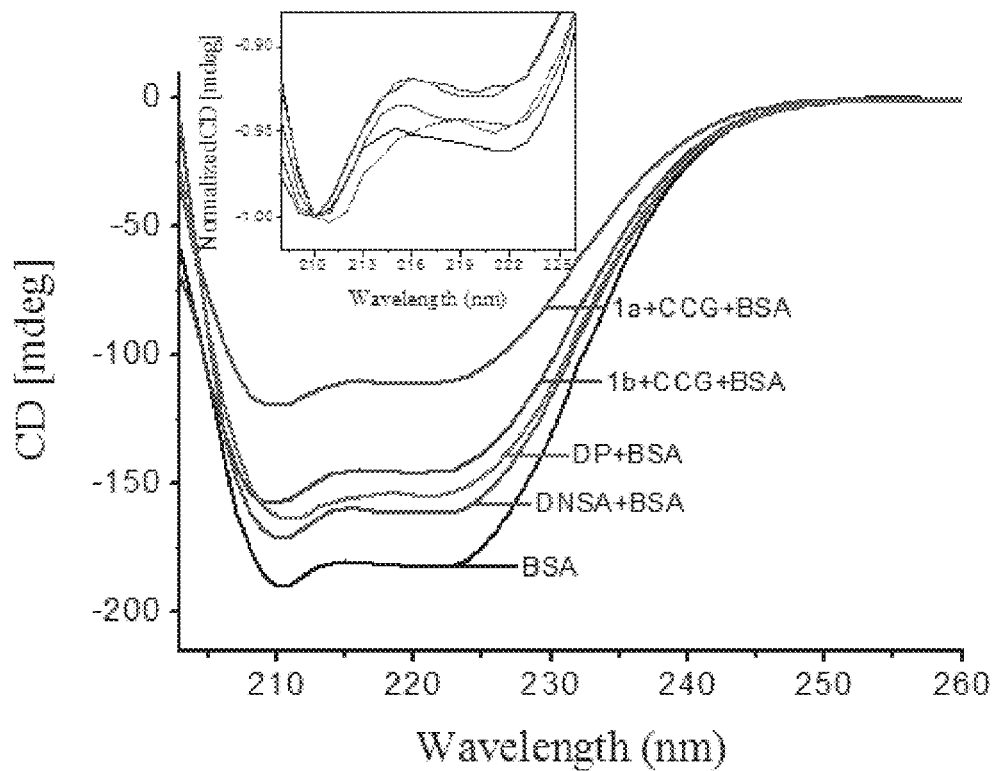
FIG. 16 shows the circular dichroism of BSA (2.5 μM) in the presence of SQ (1a-1c, 2.5 μM) and CCG (8.4 μg/mL), wherein the concentration for dansylamide (DNSA) and dansylproline (DP) is 30 μM and the inset shows partial spectra.

Circular dichroism (CD) was used to corroborate the interaction. BSA exhibits two negative bands at 208 and 222 nm, which represent the typical a-helix structure of protein (FIG. 16). After the addition of SQ/CCG, the intensity of negative bands decreases regularly, indicating that the binding of SQ/CCG can change the secondary structure of BSA, especially a-helix structure. The complex formation between SQ/CCG and BSA was further confirmed by red-shift of BSA peak. BSA might be partially associated to CCG as shown in FIG. 14, as CCG is known to exhibit high nonspecific affinity to biomacromolecules such as protein and DNA. It should be pointed to that the association between BSA and CCG might occur only at the local level without formation of an extended network.

In conclusion, CCG was found to modulate the aggregate structure and to tune the hydrophobicity of SQ dye. Without CCG, SQ exhibited weak or no response to BSA. Addition of BSA protein to SQ-CCG led to drastic fluorescence turn-on (by as much as 80 fold), attributing to the improved dye delivery by CCG. Since CCG has no cytotoxicity in vivo and can serve as drug delivery carrier, the demonstrated SQ-protein interaction could be a useful tool in the development of fluorescent sensors for protein detection. Squaraine dyes are known to exhibit efficient photodynamic therapeutical applications (PDT). The possibility of using graphene to delivery the PDT drug to protein is currently being examined in our laboratories.

Experimental Results Site Selective SQ Dyes

Figure 17:
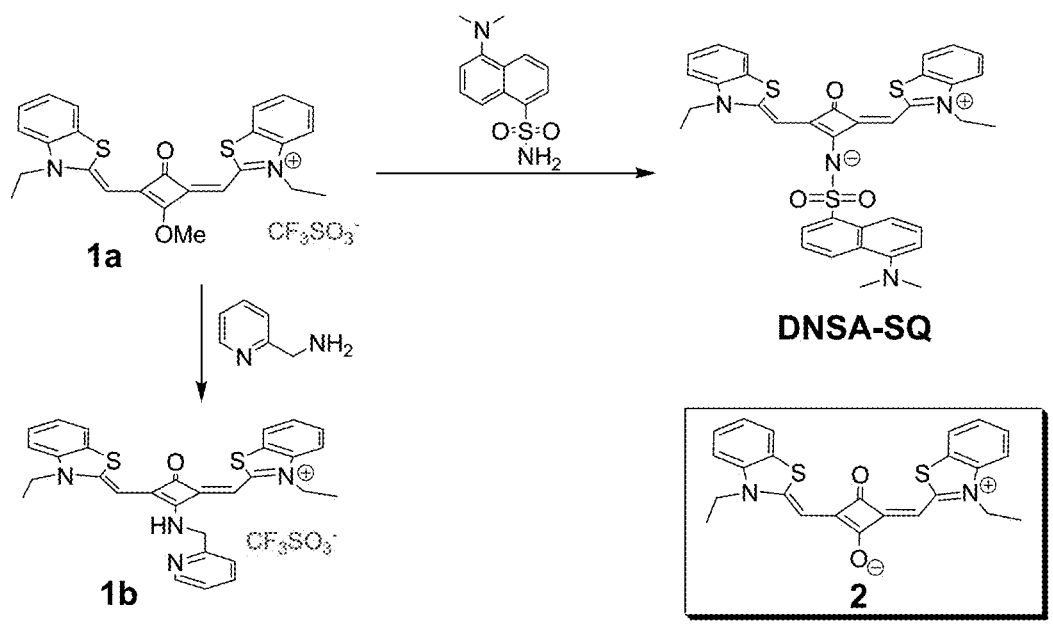
FIG. 17 shows the synthesis of DNSA-SQ and squaraine 1b.

Herein we reported a simple site-selective BSA sensor that is facile to synthesize and contains a TBET (DNSA-SQ, FIG. 17). Our result shows that the DNSA-SQ can bind specifically to site I. To the best of our knowledge, this is the first example of selective BSA sensing that is built on a TBET platform. By using travelling wave ion mobility mass spectrometry (TWIMS), a variant of ion mobility spectrometry, protein conformation was shown to change in responding to a guest molecule binding at site I or site II of BSA. In addition, DNSA-SQ exhibits adequate molecular lipophilicity for cell membrane penetration, thereby illustrating the potential for in vivo application.

DNSA-SQ was synthesized by using a modified procedure previously reported by Santos, et al where a site I selective binding ligand group dansylamide (DNSA) was attached to the squaraine ring. In the produced squaraine, a stabilized negative charge on the nitrogen was connected to the conjugated backbone bearing a positive charge. As a consequence, the molecule had a net charge of zero (i.e., zwitterionic), which reduces its dependence on protein surface charge and could facilitate the site selectivity. In comparison with the known zwitterionic salt squaraine 2 (FIG. 17), which uses an oxygen anion (—O$^-$), the zwitterion DNSA-SQ had the following advantages: (i) easy accomodation of a functional group such as DNSA; (ii) formation of zwitterion without using basic conditions (as a consequence of the stabilized anion). No fluoride signal was detected in the $^{19}$F NMR spectra of DNSA-SQ, supporting the proposed zwitterion structure which involved no counter ions ($CF_3SO_3^-$). In addition, high resolution mass of DNSA-SQ revealed the molecular weight of 664.1642, without the presence of counter anion.

The crystal structure of DNSA-SQ showed that the squaraine skeleton is nearly planar, while the dansylamide ring was twisted away and perpendicular to the squaraine plane. The molecular geometry, where the donor (aminonaphthalene) and acceptor fragments are not coplanar, provided a necessary condition for a TBET cassette. The counter ion was present in the crystal structure of 1b, but absent in that of DNSA-SQ, as anticipated.

The absorption and fluorescence of DNSA and DNSA-SQ were measured in $CH_3CN$. DNSA-SQ exhibited two absorption bands at 345 and 665 nm, corresponding to DNSA segment and squaraine skeleton respectively. Observation of both absorption bands indicated that DNSA chromophore and squaraine skeleton were not electronically connected and behaved as two separate conjugated systems. However, no DNSA segment fluorescence can be detected from DNSA-SQ when excited at 345 nm, implying close 100% energy transfer.

Figure 18:
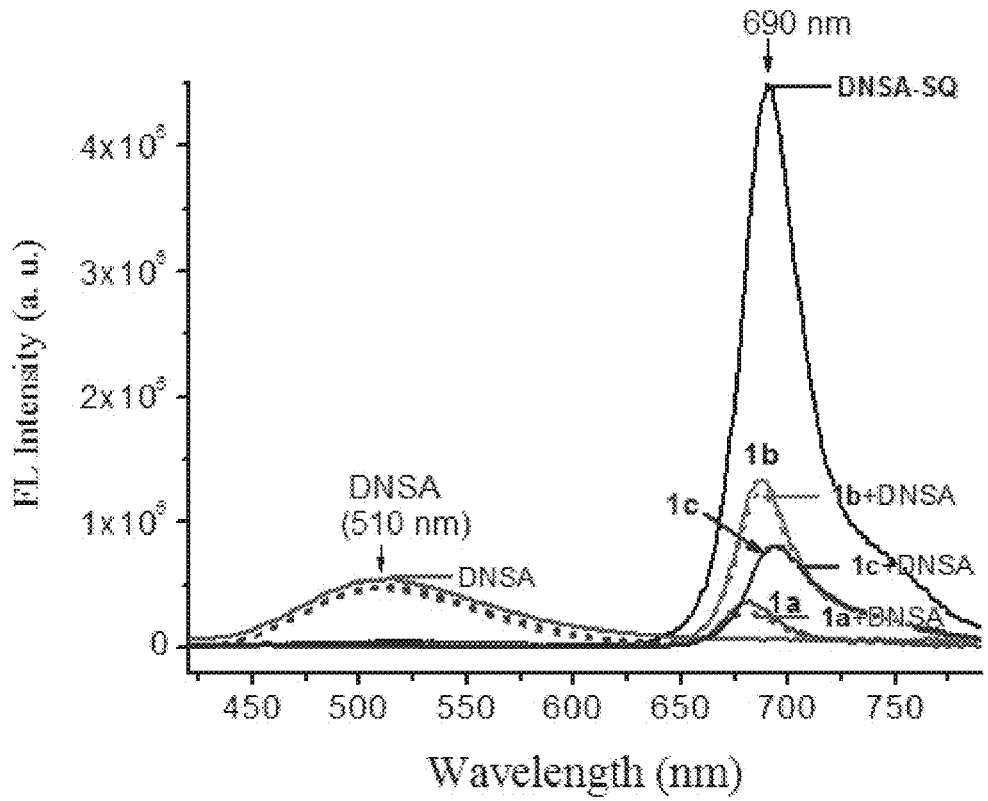
FIG. 18 shows the fluorescence of DNSA-SQ (5 μM), DNSA (5 μM) and 1a-1c (5 μM) in $CH_2Cl_2$ (Excited at 400 nm), with the spectrum of DNSA shown slightly offset for clarity.

DNSA and squaraine 1a-1c alone gave corresponding emission band at 510 nm and ~690 nm, respectively (FIG. 18). Fluorescence of DNSA-SQ however, revealed only one emission peak at 690 nm, when excited at the donor DNSA (400 nm). The emission peak at 690 nm was attributed to the acceptor of the TBET cassette DNSA-SQ. Under the same conditions ($CH_2Cl_2$, MeOH and 10 mM phosphate buffer/MeOH 3:2), the TBET cassette DNSA-SQ gave stronger fluorescence than the acceptor 1a-1c alone when excited at 400 nm. The fluorescence enhancement factors (FEFs) measured in $CH_2Cl_2$, were 12.4-, 3.3- and 5.5-fold for 1a, 1b and 1c, respectively. For comparison, the fluorescence spectra of an equimolar mixture of the donor DNSA and acceptors 1a-1c in $CH_2Cl_2$, were also examined. The 1:1 mixture of DNSA and squaraine 1a-1c revealed no visible fluorescence intensity change, indication that intermolecular energy transfer was not occurring in the mixture under the same conditions. Thus, the superiority of the TBET cassette DNSA-SQ for energy transfer is evident.

Interestingly, absorption spectrum of DNSA-SQ in aqueous or phosphate buffer solution (PBS) displayed an additional peak that is about 50 nm blue-shifted from the monomer band. The new band at 622 nm can be assigned to H-aggregate on the basis of the observed spectral shift. Addition of BSA to the solution decreased the aggregation absorption bands at 622 and 677 nm, while the ratio of intensity (A677/A622) is notably increased. The result indicates that the BSA favors to interact with squaraine dye in the monomeric form. Addition of the protein also caused the absorbance increasing at ~277 nm, which is corresponding to the tryptophan chromophore in BSA site I, and simultaneous decreasing at 351 nm with an isobestic point at around 306 nm. The result suggests that the interaction between squaraines and tryptophan chromophore located at site I of BSA, mainly involving Tr-stacking and hydrophobic interaction.

DNSA-SQ exhibited weak fluorescence in aqueous solution ($\phi_f$=1.0×10$^{-4}$), due to its high tendency to form aggregates. Interestingly, the fluorescent intensity ($\lambda_{em}$ at ~675 nm) increased significantly upon addition of BSA (fig. S10) (DNSA+3 eq BSA: $\phi_f$=4.1×10$^{-3}$). With the 1:1 binding model from fitting of absorption titration spectra, the dissociation constant for BSA was estimated to be 9.35×10$^{-6}$ M upon titration with BSA in aqueous solution. In sharp contrast, there is no response to BSA in aqueous solution for 1b, as its binding to BSA requires addition of surfactant SDS or graphene. In other words, the DNSA substituent in DNSA-SQ greatly improved the SQ dye's interaction with protein, making it a convenient tool for selective protein detection.

In responding to the BSA concentration, the fluorescence intensity at 674 nm exhibited good linear correlation over a wide concentration range (0.04-0.16 and 0.5-3 equiv). The fluorescence enhancement upon binding BSA reached over 140-fold, which was quite large in comparison with those being reported. The detection limit was 1 μg/mL of BSA (signal-to-noise ratio was 3). The fluorescence response of DNSA-SQ to other proteins in PBS was also investigated. There was no obvious fluorescence change with lysozyme, trypsin, formaldehyde dehydrogenase, lipase, chymotrypsin and fibrinogen, showing that this squaraine dye exhibits very high selectivity in responding to BSA. The observed specific binding to site I can be attributed to hydrophobic pockets of BSA in its structure.

The site-selective binding of BSA/DNSA-SQ was probed by employing a site selective binding ligand, which would result in decrease in fluorescence intensity when the squaraine dyes were displaced from a specific BSA binding site. Addition of site I binding ligand DNSA to the solution of BSA/DNSA-SQ complex did not result in fluorescence intensity change, since DNSA-SQ has stronger interaction with site I of BSA. In other words, once site I of BSA was occupied by DNSA-SQ, the dye was not replaceable by ligand DNSA from the site I. Interestingly, addition of site II binding ligand DP to a solution of the BSA/DNSA-SQ complex resulted in fluorescence intensity increasing (not decreasing), suggesting that no displacement of dye DNSA-SQ from its BSA complex. Control experiment further showed that the addition of excess DP or DNSA resulted in negligible changes in the emission of DNSA-SQ in the absence of BSA. The result indicates that the fluorescence increasing of BSA/DNSA-SQ by addition of DP was not due to the interaction between DP and DNSA-SQ dye. The observed fluorescence increasing thus implies that the BSA conformation change as DP entered the site II, which stimulated interaction of BSA/DNSA-SQ at site I. It was noted that a squaraine dye can selectively bind BSA at site I (~40%) and site II (~60%) on the assumption of no dependency between Site I and II of BSA. Circular dichroism (CD) was also used to probe the proposed binding mechanism. Similar CD spectra usually represent a similar binding mode between the sensor and protein. BSA exhibits two negative bands at 208 and 222 nm, attributing to the typical a-helix structure of protein. Under the same conditions, the effect of DNSA-SQ on the CD spectrum of BSA was similar to that of DNSA. The result further supports that DNSA-SQ was binding to site I of BSA.

Figure 19:
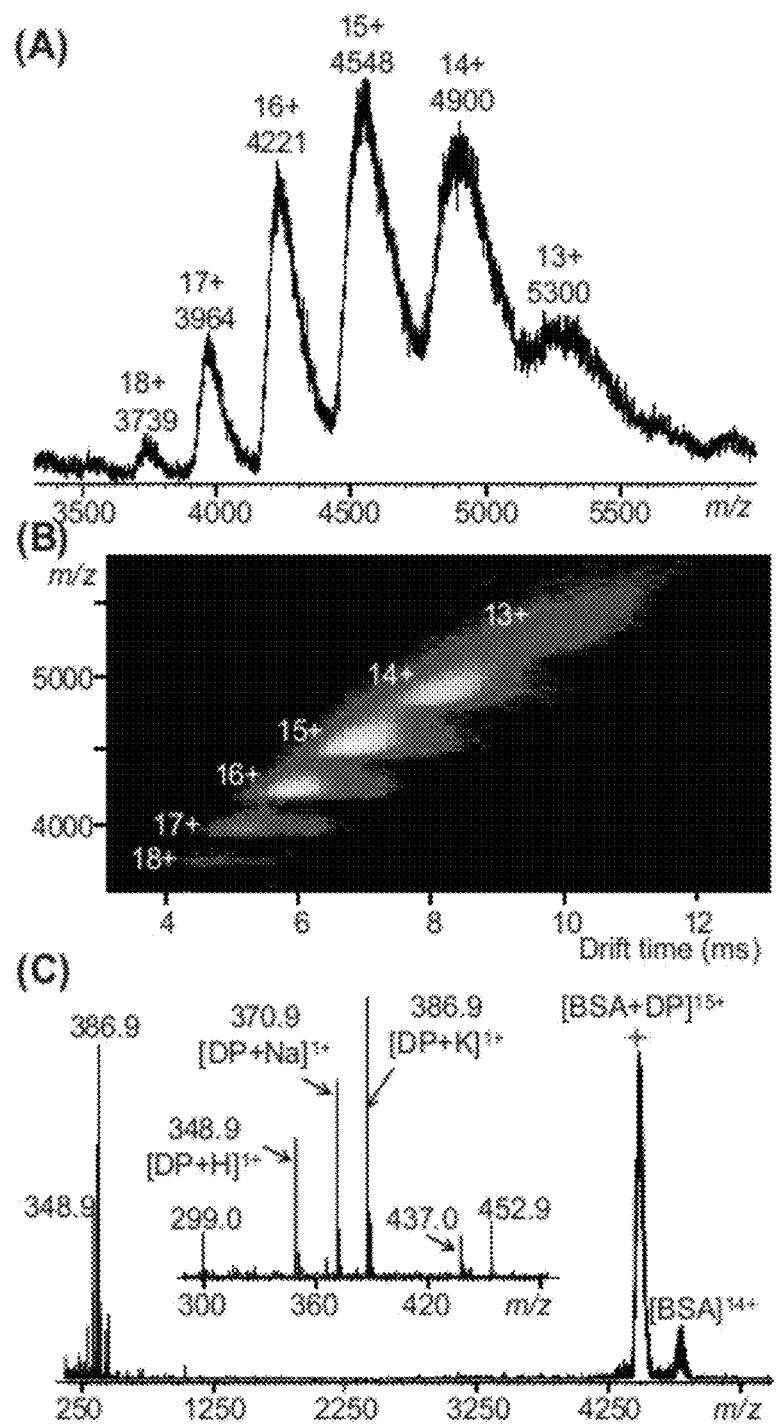
FIGS. 19(a)-(c) show conventional ESI mass spectrum of BSA+DP (FIG. 19(a)); two-dimensional ESI-TWIM MS plot (m/z vs. drift time) of BSA+DP, acquired using a traveling-wave velocity of 350 ms-1 and a traveling-wave height of 12 V (FIG. 19(b)) and tandem mass spectrum of 15+ ions of complex BSA+D (FIG. 19(c))

There is now increasing evidence to suggest that protein conformation in the gas phase mirrors those in the solution phase, particularly over short time that they exist within the mass spectrometer. Ion mobility mass spectrometry, when coupled with ESI, can produce an array of multiply charged gas-phase ions from protein molecules in solution which is related to the solution-phase folded and unfolded conformation of the protein. The structural measurement, namely, collision cross-section, can be calculated from the drift time of each ion. Herein we use travelling wave ion mobility mass spectrometry (TWIMS) to detect the change of the protein conformation after different site selective binding guests were added in BSA buffer solution. TWIMS was performed under the same conditions to ensure minimal error for compassion. The conventional ESI mass spectra and TWIMS spectra exhibited charge states in the range 13+ to 18+, corresponding to BSA or the BSA-guest complex (FIG. 19). The binding of DNSA, DP and DNSA-SQ to BSA were demonstrated through tandem MS of complex ions. As shown in FIG. 19(c), the ions of DP were generated through the tandem MS of intact complex ions at 15+. Taking 15+ charge state for example, the mobility peak drift time $t_D$=6.41, 6.80, 6.67 and 6.54 ms for BSA, BSA+DP, BSA+DNSA-SQ and BSA+DNSA, respectively. The corresponding experimental collision cross-sections (CCS) are 4298, 4364, 4342 and 4320 Å2 using standard curve. The experimental collision cross-sections of BSA and its binding complexes were plotted for different charge states, and the cross-section of BSA+DP was significantly larger than BSA alone and two BSA/DNSA species, corresponding to a more extended structure. This result suggests that DP binding at site II induces a notable expansion in BSA conformation. This finding is consistent with the fluorescence change discussed above, particularly for the fluorescence enhancement by adding DP to BSA/DNSA-SQ. The observation clearly indicates that binding at the site I and II of BSA is related to each other to some extent, which is previously assumed to operate independently.

Figure 20:
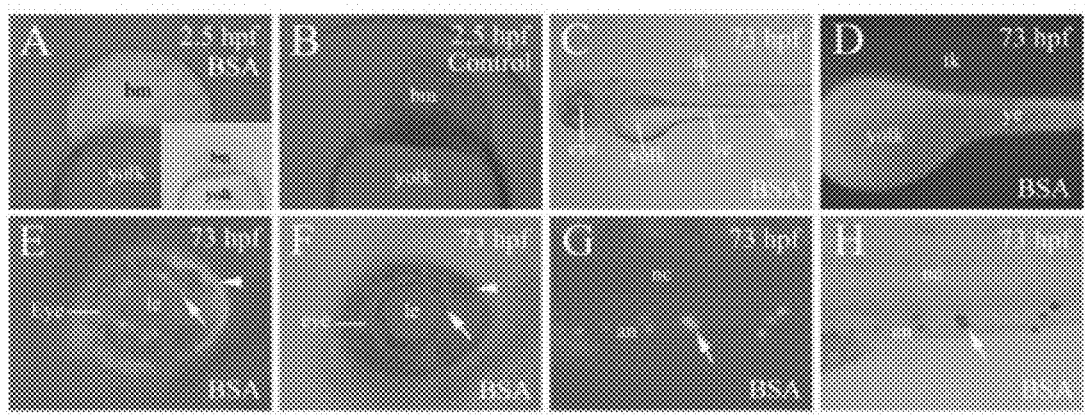
FIG. 20 provides panels A-H (photographs) that show DNSA-SQ labeling of live developing zebrafish wherein: panel A and B show embryos of 2.5 hpf with dorsal side up; all blastomeres (bm) are labeled in a BSA injected embryo (panel A); the insert in panel A shows the same embryo under bright field microscopy; panel B shows that none of the blastomeres is labeled in an uninjected control embryo (panel B); panels C—H are from 73 hpf embryos injected with BSA, all showing lateral views with anterior to the left and dorsal up; panel C is an image of an almost entire embryo for orientation purpose; panel D shows strongly labeled yolk and yolk extension (ye); panels E and F show the same eye under both fluorescent and bright field microscopy, with bright field light intensity much lower for panel E than panel F; arrows and arrowheads in the two panels point to the same regions, respectively; panel G shows labeled pigmented cells near the anus (an) region; panel H is from the same region shown in panel G, but under bright filed microscopy; the arrows in panels G and H point to the same two pigmented cells; and other abbreviations used include le=lens, nc=notochord and tk=body trunk.

The most attractive application for protein sensing is labeling and imaging in living organisms. Zebrafish have recently become an important model organism for the study of vertebrate imaging. This is because the embryos of zebrafish are transparent, allowing for clear observation of their organs without the need for dissection. The optical transparancy of zebrafish, therefore, provides a convenient organism for detection of ions by fluorescence microscopy. No published reports are found on the use of zebrafish for BSA fluorescence microscopy. Herein, DNSA-SQ was examined in developing zebrafish for its applicability. DNSA-SQ labeling was examined in developing zebrafish by adding DNSA-SQ to fish tank water (treatment lasted for one hour at room temperature). There was no labeling in control (i.e. without BSA supplement) embryos at 2.5 hours post fertilization (hpf, FIG. 20B), 36 hpf and 73 hpf (data not shown). However, injection of BSA to 1-4 cell stage zebrafish embryos (2-4 nl/embryo), followed by DNSA-SQ labeling resulted in labeling of all dividing cells (blatomeres) at 2.5 hpf (FIG. 20A), and confined BSA labeling at 73 hpf (FIG. 20D-H). At 73 hpf, the labeling was detected in the yolk and yolk extension (FIG. 20D), eye (FIG. 20E) and pigmented cells in the body trunk and tail regions (FIGS. 20G and H). Closer examination of the eye revealed that most of the labeling in the eye was within pigmented regions of the eye (FIGS. 20E and F). The DNSA-SQ labeling pattern show good biocompatibility, excellent turn-on fluorescence.

All DNSA-SQ treated embryos/larvae appeared normal in size and shape compared to untreated embryos/larvae from the same breeding. Therefore DNSA-SQ was proving not toxic to the subjects. Non-toxicity, cell permeability and NIR emission suggested that DNSA-SQ could also be used for in vivo BSA sensing in other organisms that are not optically transparent. At present, commercially available NIR fluorophores are typically hydrophobic and/or di-/tetra-sulfonated, which restrict their wide application for in vivo imaging. The developed DNSA-SQ which exhibits a balanced charge with a net charge of zero (i.e., zwitterionic), could shield its underlying hydrophobicity while providing certain water solubility, thereby rendering its in vivo behavior.

In summary, a novel zwitterionic squaraine TBET probe was designed and synthesized, which can selectively detect BSA in aqueous medium with near infrared turn-on fluorescence (by about 140-fold). The key feature of the novel class of TBET platform include large pseudo-Stokes shift (up to 340 nm). In addition, the developed DNSA-SQ interacts with BSA selectively at the site I. The improved interaction with proteins, via introducing DNSA substituent, makes the squaraine dyes potentially useful probes for selective protein recognition. Interestingly, DNSA-SQ can easily penetrate through cell membranes for in vivo applications during the development of living zebrafish embryos. The developed probe thus could be a potentially useful tool for noncovalently labeling of protein in biology.

Using ESI-TWIMS-MS, the BSA conformation shows significant change after binding of displacement reagent DP at site II in buffer solution. On the basis of displacement by site-selective ligands and mass spectra data, DNSA-SQ enters selectively at site I, whose fluorescence is influenced by binding of DP at site II. Comparison of site I and site II binding shows that the latter induces a larger conformational response on BSA protein conformation than the former. The response of a fluorescence probe at a specific site (such as site I), therefore, could also shed some light on the binding of the other site (e.g. site II). Study of this synergetic interaction between two binding sites could lead to improved understanding on the protein-dye interaction.

What is claimed is:

1. A method for the detection of protein comprising the steps of:
preparing an aqueous dye solution comprising aggregated squaraine dyes by combining squaraine dyes and an aggregation agent selected from an anionic surfactant and graphene oxide, where the aggregation agent serves to promote the formation of aggregates of the squaraine dyes in the aqueous dye solution,
joining the aqueous dye solution with a test sample including a protein to prepare a test solution, and
exciting the test solution at a wavelength of about 635 nm to about 650 nm.

2. The method of claim 1, where the aggregation agent is an anionic surfactant.

3. The method of claim 2, where the anionic surfactant is selected from the group consisting of sodium dodecyl sulfate (SDS), sodium dodecyl benzene sulfonate (SDBS), tetraethylammonium dodecylbenzenesulfonate (DBS), and dioctyl sodium sulfosuccinate (DSS).

4. The method of claim 1, where the aggregation agent is graphene oxide.

5. The method of claim 1, where the squaraine dyes include a squaraine dye defined by the formula:

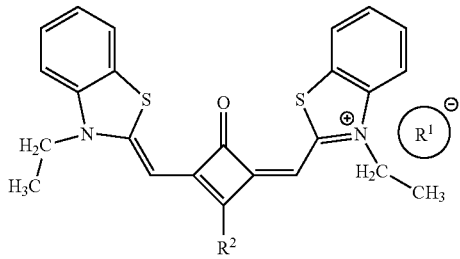

wherein $R^1$ is a counterion and $R^2$ is selected from the group consisting of:

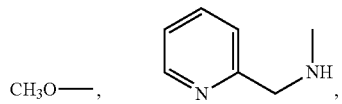

6. The method of claim 5, where the counter ion is selected from the group consisting of trifluoromethanesulfonate ($CF_3SO_3^-$) and iodide ($I^-$).

7. The method of claim 1, where the squaraine dyes include a squaraine dye defined by the formula:

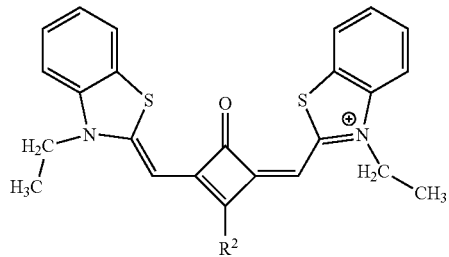

wherein $R^2$ is selected from the group consisting of

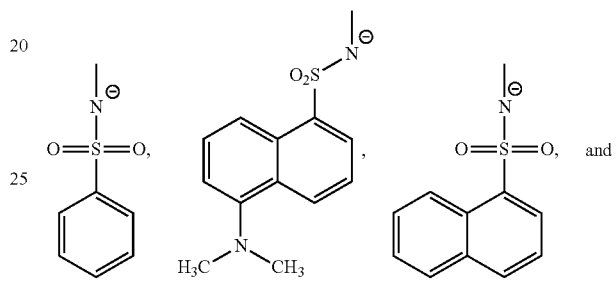

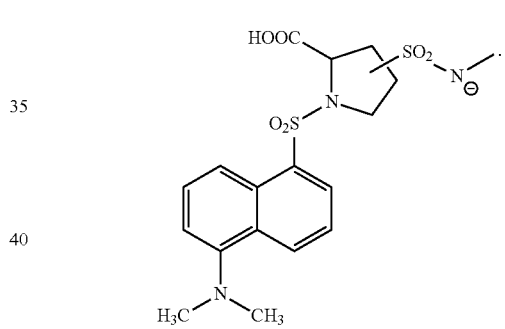

8. A method for the detection of protein comprising the steps of:
preparing test solution that includes protein and aggregated squaraine dyes prepared by combining squaraine dyes and an aggregation agent selected from anionic surfactants and graphene oxide;
exciting the test solution, and
detecting a fluorescent response.

9. The method of claim 8, where the step of exciting the test solution is performed using an excitation wavelength that is between 400 and 700 nanometers.

10. A method for the detection of protein comprising the steps of:
preparing an aqueous dye solution comprising aggregated squaraine dyes by combining squaraine dyes and an aggregation agent,
joining the aqueous dye solution with a test sample including a protein to prepare a test solution, and
exciting the test solution at a wavelength of about 635 nm to about 650 nm; where the squaraine dyes include a squaraine dye defined by the formula:

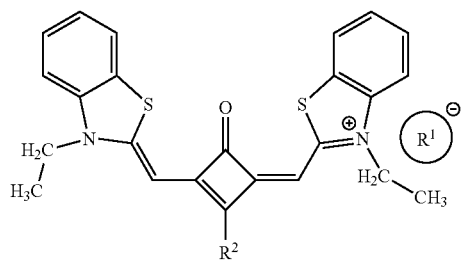

wherein R¹ is a counterion and R² is selected from the group consisting of:

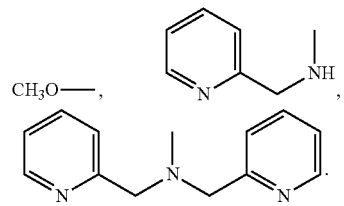

or where the squaraine dyes include a squaraine dye defined by the formula:

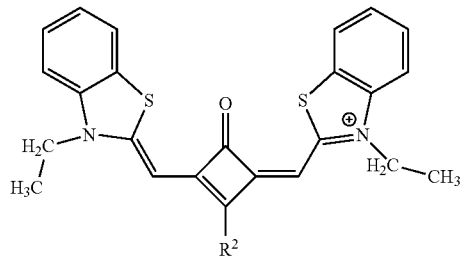

wherein R² is selected from the group consisting of

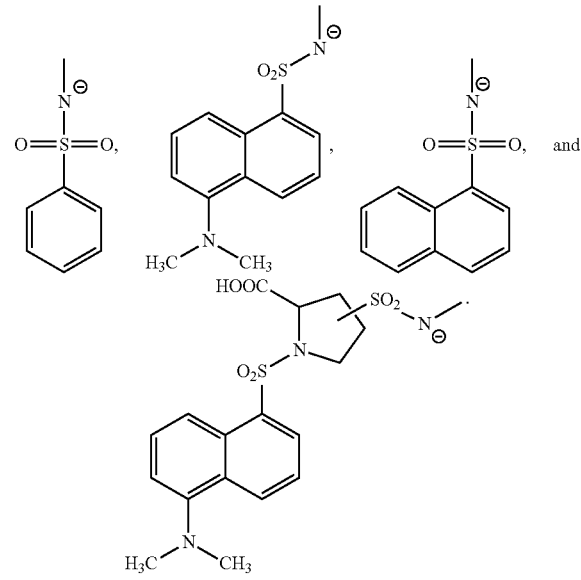

11. The method of claim 10, where the squaraine dyes include a squaraine dye defined by the formula:

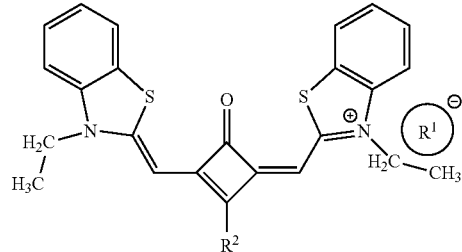

wherein R¹ is a counterion and R² is selected from the group consisting of:

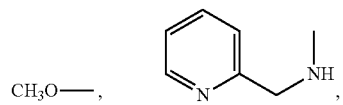

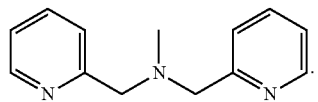

12. The method of claim 11, where the counter ion is selected from the group consisting of trifluoromethanesulfonate ($CF_3SO_3^-$) and iodide ($I^-$).

13. The method of claim 10, where the squaraine dyes include a squaraine dye defined by the formula:

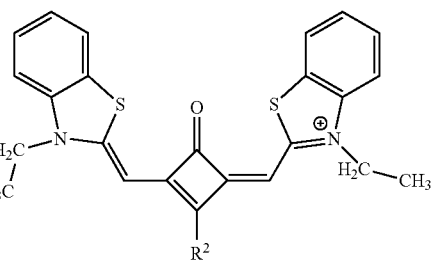

wherein R² is selected from the group consisting of

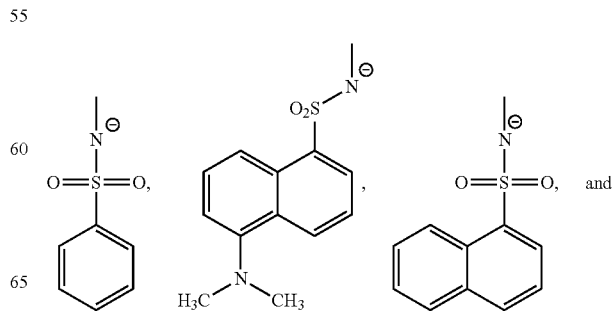

-continued
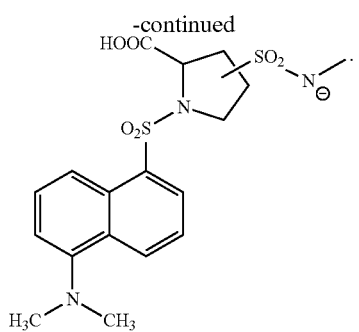
14. The method of claim 10, where the aggregation agent is an anionic surfactant.
15. The method of claim 10, where the aggregation agent is graphene oxide.
* * * * *